United States Patent [19]
Fujita

[11] Patent Number: 5,713,137
[45] Date of Patent: *Feb. 3, 1998

[54] APPARATUS FOR DEODORIZING, STERILIZING AND DRYING BEDDING AND CLOTHING

[76] Inventor: Sanai Fujita, 107 Green Park Kotesashi, 12-1, 4-chome, Kotesashi-cho, Tokorozawa-shi, Saitama-ken, Japan

[*] Notice: The term of this patent shall not extend beyond the expiration date of Pat. No. 5,514,346.

[21] Appl. No.: 639,827

[22] Filed: Apr. 29, 1996

[30] Foreign Application Priority Data

| May 17, 1995 | [JP] | Japan | 7-141387 |
| May 17, 1995 | [JP] | Japan | 7-141388 |
| May 17, 1995 | [JP] | Japan | 7-141389 |

[51] Int. Cl.$^6$ ................................. F26B 25/00
[52] U.S. Cl. ............... 34/106; 34/202; 422/122; 422/124; 422/306
[58] Field of Search ................. 34/60, 61, 85, 34/90, 104, 106, 107, 619, 621, 622, 168, 174, 175, 176, 202, 215, 232, 239; 422/124, 122, 306

[56] References Cited

U.S. PATENT DOCUMENTS

| 4,625,432 | 12/1986 | Baltes | 34/202 X |
| 4,677,764 | 7/1987 | Cerny | 34/202 X |
| 5,173,258 | 12/1992 | Childers | 422/27 |
| 5,412,928 | 5/1995 | Reithel | 34/104 |
| 5,514,346 | 5/1996 | Fujita | 422/124 |

*Primary Examiner*—John M. Sollecito
*Assistant Examiner*—Steve Gravini
*Attorney, Agent, or Firm*—Andrus, Sceales, Starke & Sawall

[57] ABSTRACT

According to the present invention, provided is a deodorization, sterilization and drying apparatus for bedding and clothing, which comprises: a warm air generator wherein an alkaline chlorine dioxide gas generator, within which is an alkaline ceramic body that is impregnated with an alkaline chlorine dioxide solution, is located along a flow path of the warm air that is generated in the warm air generator; an air mattress, a case and a bag for deodorizing, sterilizing and drying bedding and clothing by using the warm air from the warm air generator; and a hose for connecting the air mattress, etc., to the warm air generator, whereby the warm air from the warm air generator is brought into contact with the ceramic body so as to supply warm air that contains alkaline chlorine dioxide gas to the air mattress, etc. In addition to the above described arrangement, provided is a deodorization, sterilization and drying apparatus for bedding, etc., which comprises an air-permeable cover that covers the air mattress and the bedclothes, and a warm air filter for filtering the warm air after deodorization, sterilization and drying are completed, and for discharging the filtered air to the outside.

29 Claims, 21 Drawing Sheets

| TEST ORGANISMS | PROCESSING TIME | 0 | 0.5 | 1 | 3 |
|---|---|---|---|---|---|
| Staphylococcus aureus ATCC25923 | LIVING ORGANISM COUNT (CFU) | $3.5 \times 10^4$ | $1.4 \times 10^3$ | $<1.0 \times 10^1$ | $<1.0 \times 10^1$ |
|  | SURVIVAL RATIO (%) | 100 | 4.0 | — | — |
| Escherichia coli NIHJ JC-2 | LIVING ORGANISM COUNT (CFU) | $2.0 \times 10^5$ | $2.5 \times 10^4$ | $<1.0 \times 10^1$ | $<1.0 \times 10^1$ |
|  | SURVIVAL RATIO (%) | 100 | 12.5 | — | — |

FIG. 17

| | BEFORE ACTIVATION | 20 MINUTES LATER | 1 HOUR LATER | 2 HOURS LATER | 3 HOURS LATER |
|---|---|---|---|---|---|
| ANALYTE 1) | − | − | − | − | − |
| ANALYTE 2) | − | − | − | − | − |

− : NO COLOR REACTION DETECTED

F I G. 1 8

APPARATUS FOR DEODORIZING, STERILIZING AND DRYING BEDDING AND CLOTHING

BACKGROUND OF THE INVENTION

1. Field of the Invention

The present invention relates to an apparatus that introduces deodorized and sterilized warm air, which contains an alkaline chlorine dioxide gas, into an air mattress, or into a case or a bag employed for deodorization, sterilization and drying, in order to dry, deodorize, and sterilize common bedding and bedclothes, such as comforters, bed sheets and pillows, and articles of clothing, worn by doctors, nurses and patients, that are used in hospitals and other medical institutions.

2. Related Arts

Conventionally provided is a bedding dryer that, as is shown in FIG. 19, supplies warm air from a warm air generator 1 through a hose 2 to an air-permeable air mattress 3, which is inserted between a mattress 5a and a coverlet 5b, and dries the mattress 5a and the coverlet 5b by using the warm air that is discharged from openings in the air mattress 3.

For such a bedding dryer, the air from the warm air generator 1 is maintained at a temperature of 50° C. or higher in order to kill ticks.

With this conventional bedding dryer, however, as part of the warm air that flows through the openings in the air mattress 3 escapes from the bedding to the outside and does not contact the mattress 5a and the coverlet 5b, all the bedclothes can not be dried completely, and all of the ticks can not be killed.

Thus, a bedding dryer has been proposed wherein, as is shown in FIG. 20, an air mattress 3a is located between a floor and a mattress 5a, another air mattress 3b is located between the mattress 5b and a coverlet 5b, and a replaceable deodorizing sheet 20 is inserted under the air mattress 3b to deodorize the mattress 5a (Japanese Unexamined Patent Publication No. Hei 5-8790).

With this kind of conventional bedding dryer, however, the air used to destroy ticks must be transmitted from the warm air generator 1 at a high temperature and for a long time, and as this may damage the material of the bedding, all the bedclothes shown can not be deodorized at the same time.

As a consequence, there is no conventional bedding dryer having a simple structure that is capable of drying bedclothes within a short time, while at the same time performing deodorization and destroying ticks, the dermatophytes that cause tinia pedis, etc.

There are some conventional laundry dryers that employ electricity or gas to dry clothing indoors on rainy days, or in rooms where no sunlight enters; but as these dryers are designed for permanent indoor installation and are difficult to move, and as generally they tend to be large, they are not convenient to use.

An easy-to-use device has therefore been proposed that, as is shown in FIG. 21, supplies warm air from an electric dryer 131 through a hose 132 to a drying bag 133 to dry clothing placed inside the drying bag 133 (Japanese Unexamined Utility Model Publication No. Hei 5-13399).

This device, however, merely dries clothing; it can neither remove from clothing the scents of perfumes nor the odor of sweat, nor can it kill dermatophytes that cause tinia pedis, etc.

Another bedding drier has been proposed that to kill ticks increases the temperature of the air from a warm air generator to 50° C. or higher (for example, Japanese Unexamined Patent Publication No. Hei 5-68790). However, with this conventional bedding drier, air to kill ticks must be supplied from the warm air generator at a high temperature and for a long time, and when this device is employed for drying clothing, the material of the clothing may be damaged.

As is described above, there is no clothing dryer having a simple structure that can dry clothing while at the same time performing deodorization, and sterilization to destroy the dermatophytes that cause tinia pedis and pathogenic bacteria.

There is a demand for a device that can not only dry clothing and bedclothes, but can also remove perfume scents and body odors from clothing, pillows and bedclothes, and that can deodorize and sterilize clothing and pillows that are used by patients and staff members in hospitals.

Lately, viral infections, etc., have become a big problem in hospitals. In particular, malignant MRSA has become a serious problem. MRSA, or *staphylococcus aureus*, is resistant to antibiotics; and as medicine is therefore ineffective against it, providing treatment for a person who has contracted this disease is difficult.

Further, as the number of home-care patients has increased recently, protection from the above infection is indispensable not only for hospitals but also for the families that provide care for home-care patients.

Protection against infections caused by viruses and MRSA is a very important matter. Conventionally, several countermeasures have been taken: avoidance of physical contact with infected persons; wearing of masks; washing of hands in an antiseptic solution after having had physical contact with infected persons or after leaving the presence of infected persons; and gargling with popidon iodine solution.

Furthermore, mattresses, bed sheets, and the clothing of patients with infectious diseases and patients who are confined to bed for a long time become soiled, and in them bad odors are generated. These items must be kept clean, and besides being washed and dried, must be deodorized and sterilized.

Actually, however, mattresses, bed sheets, and the clothing of patients are simply washed and dried, and no effective measures are taken to protect against the indirect transmission of infections via mattresses, etc. Thus, a method and an apparatus are needed for the easy deodorization, sterilization, and drying of the bedding and the clothing of patients having infectious diseases, as well as those of other patients.

SUMMARY OF THE INVENTION

It is one object of the present invention to provide an apparatus having a simple structure that can perform, within a short time, deodorization, the destruction of ticks, sterilization to destroy pathogenic bacteria and dermatophytes, and drying for ordinary bedding and clothing and for the bedding and clothing that is used and worn by doctors and patients in medical institutions.

According to a first invention, provided is a deodorization, sterilization and drying apparatus for bedding, which, as is shown in FIGS. 1 through 4, comprises:

a warm air generator 1 wherein are provided a warm air nozzle 10, a heater 11 and a fan 12, and wherein an alkaline chlorine dioxide gas generator 13, within which is an alkaline ceramic body 14 that is impregnated with an alkaline chlorine dioxide solution, is located along a flow path of the warm air that is generated in the warm air generator 1, an air-permeable air mattress 3 from which the warm air from the warm air generator 1 is ejected to dry bedclothes 5a and 5b, and a hose 2 for connecting the air mattress 3 to the warm air generator 1, whereby the warm air from the warm air generator 1 is brought into contact with the ceramic body 14 so as to supply warm air that contains alkaline chlorine dioxide gas to the air mattress 3.

In addition to the above described arrangement, a deodorization, sterilization and drying apparatus for bedding according to the first invention further comprises an air-permeable cover 4 that covers the air mattress 3 and the bedclothes 5a and 5b.

According to a second invention, provided is a deodorization, sterilization and drying apparatus for clothing and bedding, which as is shown in FIGS. 5 through 9, comprises:

- a deodorization, sterilization, and drying case 103, for clothing and bedding, that is freely opened and closed, wherein are provided air outlets 111, a clothing rod 112, and a warm air pipe 113 in which warm air ejection holes 114 are formed,
- a warm air generator 1 wherein are provided a warm air nozzle 10, a heater 11 and a fan 12, and wherein an alkaline chlorine dioxide gas generator 13, within which is an alkaline ceramic body 14 that is impregnated with an alkaline chlorine dioxide solution, is located along a flow path of the warm air that is generated by the warm air generator 1, and
- a hose 2 for connecting the warm air pipe 113 of the deodorization, sterilization and drying case 103 to the warm air generator 1, whereby the warm air from the warm air generator 1 is brought into contact with the ceramic body 14 so as to supply warm air that contains alkaline chlorine dioxide gas to the deodorization, sterilization and drying case 103.

According to the first and the second inventions, the alkaline chlorine dioxide solution that is used to permeate the ceramic body, which is impregnated with the alkaline chlorine dioxide solution, has a calculated chlorine dioxide content of 50 ppm to 1000 ppm.

According to a third invention, a deodorization, sterilization and drying apparatus for medical bedding that, as is shown in FIGS. 10 and 11, comprises:

- a warm air generator 1 that includes a fan 12, a heater 11, and an alkaline chlorine dioxide gas generator 13 in which is provided a ceramic body 14 that is impregnated with an alkaline chlorine dioxide solution;
- a non-air-permeable bag 203, which is freely opened and closed and inside which bedclothes are retained for deodorization, sterilization, and drying;
- a warm air supply pipe 221, along which warm air that contains alkaline chlorine dioxide gas is supplied from the warm air generator 1, the warm air being injected into the bag 203 through a plurality of warm air injection holes 222 that are formed in the warm air supply pipe toward the inside of the bag 203;
- a warm air absorption pipe 224 for absorbing the warm air after bedclothes in the bag 203 are deodorized, sterilized and dried; and
- a warm air filter 204, which has a replaceable filter medium 231 and a replaceable adjusting filter medium 232, for filtering the warm air that is directed through the warm air absorption pipe 224 after deodorization, sterilization and drying are completed, and for discharging the filtered air to the outside.

According to the third invention, the alkaline chlorine dioxide solution that is used to permeate the ceramic body 14, which is impregnated with the alkaline chlorine dioxide solution, has a calculated chlorine dioxide content of 500 ppm to 3000 ppm.

According to the third invention, the filter medium 231, which is replaceably provided in the warm air filter 204, consists of non-woven cloth or activated carbon, and the adjusting filter medium 232 consists of ceramic particles 233.

The alkaline chlorine dioxide gas generator 13 is stored detachably in the warm air generator 1.

The alkaline chlorine dioxide gas generator 13 is installed outside the warm air generator 1 and is so connected to the hose 2 as to be detachable.

As is shown in FIG. 13, a unit 15 for supplying an alkaline chlorine dioxide solution to the ceramic body 14 is detachably attached to the alkaline chlorine dioxide gas generator 13, and formed in the ceramic body 14 is a solution supply groove 16 for supplying the alkaline chlorine dioxide solution to a surrounding side portion of the ceramic body 14.

As is shown in FIGS. 14 and 15, the alkaline ceramic body 14 is columnar in shape, and in cross section has a plurality of longitudinal through holes 17 and 18.

The alkaline ceramics contains at least one material selected from a group consisting of animal bone powder, shell powder, limestone powder, and coral powder.

The alkaline ceramic body 14 is formed of animal bone powder as the main activated element, and contains at least one ceramic selected from a group consisting of silica gel, alumina, and zeolite.

As is described above, according to the first invention, the alkaline chlorine dioxide gas generator 13 is located along the warm air flow path from the warm air generator 1. The warm air that is generated by the warm air generator 1 is brought into contact with the ceramic body 14, which is internally provided in the alkaline chlorine dioxide gas generator 13, so as to supply warm air that contains alkaline chlorine dioxide gas for deodorization and sterilization to the air mattress 3.

As air that is driven by the fan 12 and is heated by the heater 11, e.g., warm air at 40° C. to 70° C., passes through the ceramic body 14 that is impregnated with an alkaline chlorine dioxide solution, alkaline chlorine dioxide gas is generated, and warm air that contains that gas passes through the hose 2 and is finally ejected from the air-permeable air mattress 3.

In addition, according to the first invention, the air-permeable cover 4 for covering the air mattress 3 and bedding is provided in order to fully and uniformly deodorize, sterilize, and dry bedclothes.

The above described air stream is blown into the targeted bedclothes, such as coverlets, pillows and clothing, in the air-permeable cover 4, so that by using a simple device the bedding and clothing can be deodorized, sterilized and dried while all ticks, etc., are killed.

According to the second invention, warm air, which is generated by the warm air generator 1 and which contains alkaline chlorine dioxide gas, is transmitted through the hose 2 to the warm air pipe 113, which is disposed around the interior of the deodorization, sterilization and drying case 103. The warm air that contains alkaline chlorine dioxide gas is discharged into the case 103 through a plurality of warm air ejection holes 114, which are formed in the warm air pipe 113, and fills the case 103.

After the zippers 115 are opened, clothing to be processed is directly hung across a rod 112 in the case 103 or it is arranged on a hanger and the hanger is then hooked over the rod 112. The zippers 115 are pulled up to close the drying case 103.

Warm air that contains alkaline chlorine dioxide gas fills the drying case 103 and ensures that the clothing in the case 103 will be dried at the same time that it is deodorized and sterilized.

Alkaline chlorine dioxide gas that overflows from the deodorization, sterilization and drying case 103 is discharged externally through the air outlets 111. The discharged alkaline chlorine dioxide gas is harmless and purifies the atmosphere.

According to this invention, the drying case 103, the warm air generator 1 and the hose 2 can be separated. The drying case 103 can be set up on a veranda, or in a warehouse, an outhouse or a laundry area, and can be connected to the warm air generator 1 and the hose 2 when it is to be used.

Therefore, a number of locations can be selected for the installation of this apparatus, and it can be installed not only at a home but also in various facilities, such as hospitals, health centers and laboratories. Further, as this apparatus has a simple structure, it is easily disassembled or assembled, and it is easy to transport this device to and to store it at the place of installation.

According to the third invention, heated air that is transmitted from the fan 12 and heater 11 contacts the ceramic body 14, which is internally provided in the alkaline chlorine dioxide gas generator 13, so that warm air that contains alkaline chlorine dioxide gas for deodorization and sterilization is supplied to the deodorization, sterilization and drying bag 203.

Air that is heated to, for example, 40° C. to 70° C. is passed through the ceramic body 14 that is impregnated with an alkaline chlorine dioxide solution. Alkaline chlorine dioxide gas is thus generated, and warm air that contains that gas is transmitted to the warm air pipe 221 and ejected through the warm air ejection holes 222, which are formed in the warm air pipe 221.

Warm air that contains alkaline chlorine dioxide gas is discharged from the warm air ejection holes 222 and is blown toward objects to be processed, such as coverlets, pillows and clothing, that are retained in the non air-permeable bag 203.

The warm air, after the objects have been deodorized, sterilized and dried, is transmitted through the warm air absorption pipe 224, filtered, and adjusted by the warm air filter 204 so that it has a neutral pH value of pH 6 to pH 7, and is finally discharged to the outside. The discharged air does not pollute the atmosphere and is harmless to humans.

According to this invention, therefore, bedding and clothing that are used in medical institutions can be completely deodorized, sterilized, and dried. Further, since warm air that is discharged from the apparatus of the invention is harmless, the apparatus can be installed in patients' rooms in hospitals, and bedclothes, such as mattresses, that are used in medical institutions, and patients' clothing can be easily deodorized, sterilized and dried at the same time.

The chlorine dioxide gas has a strong sterilization and deodorization effect; the alkaline gas accelerates drying and provides protection from molds as well as aiding sterilization; and the heated air provides the drying effect for objects. The present invention utilizes the synergistic effect acquired by employing together chlorine dioxide gas, alkaline gas and warm air.

As a result, according to the apparatus of the present invention, warm air for deodorization and sterilization can be surely and easily provided, so that the killing of ticks and disease germs, the prevention of molds, and the deodorization, sterilization and drying of objects is ensured.

BRIEF DESCRIPTION OF THE DRAWINGS

FIG. 17 is a diagram showing the results of the measurements to determine the number of living germs when the experiment was conducted by using the model in FIG. 16;

FIG. 18 is a diagram showing the results of the measurements to determine the remaining amount of chlorine dioxide when the experiment was conducted by using the model in FIG. 16;

DETAILED DESCRIPTION OF THE PREFERRED EMBODIMENTS

The preferred embodiments of the present invention will now be described while referring to the accompanying drawings. The present invention is, however, not limited to these embodiments.

Figure 1:
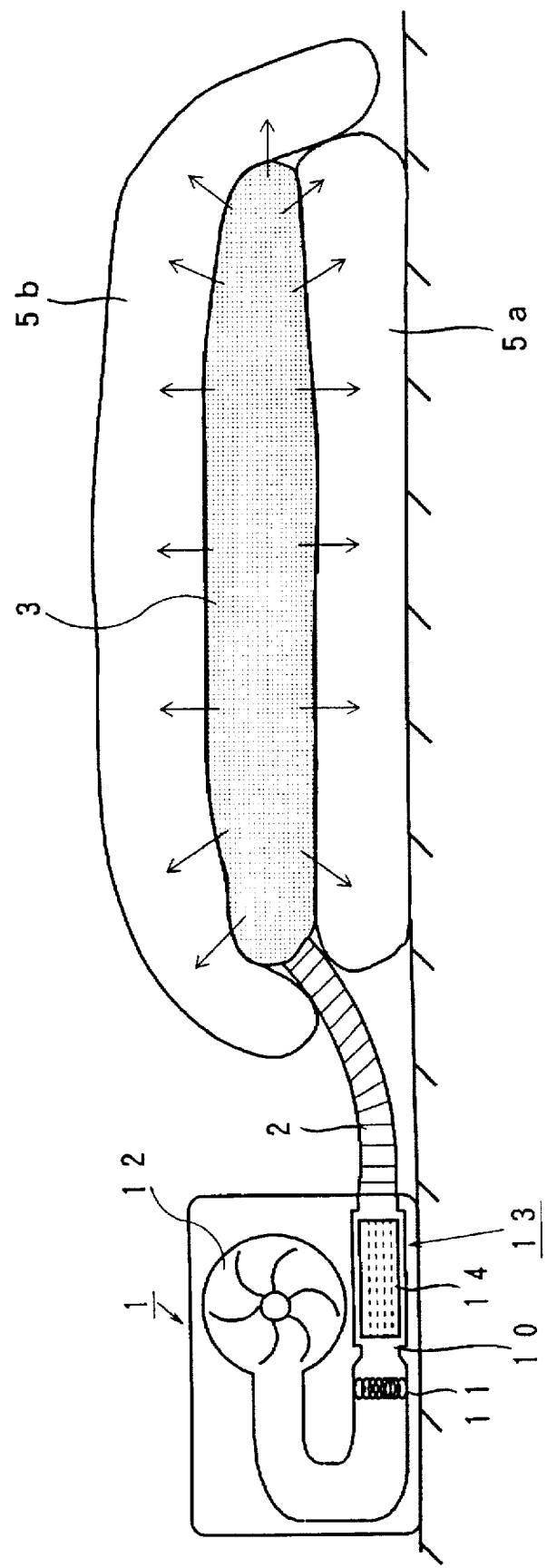
FIG. 1 is a diagram illustrating the arrangement of a first embodiment of an apparatus according to a first invention.
Figure 2:
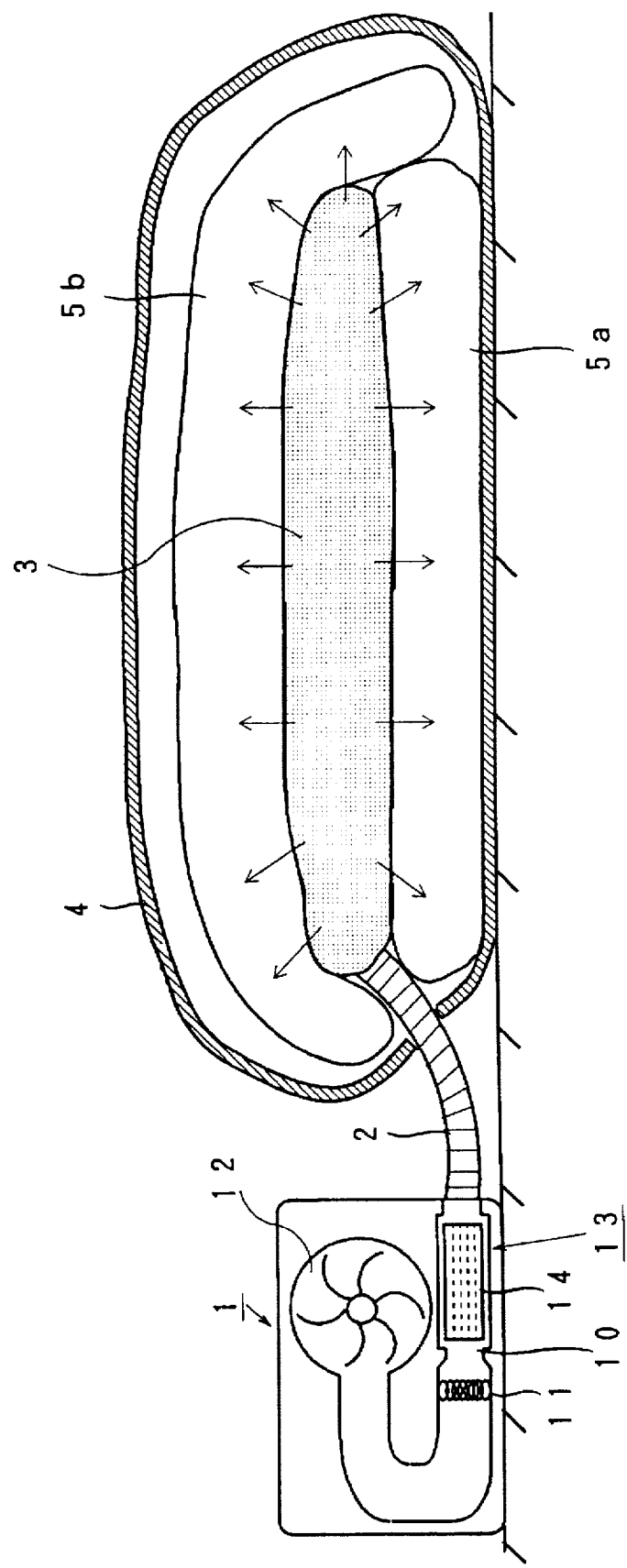
FIG. 2 is a diagram illustrating the arrangement of a second embodiment of the apparatus according to the first invention.
Figure 3:
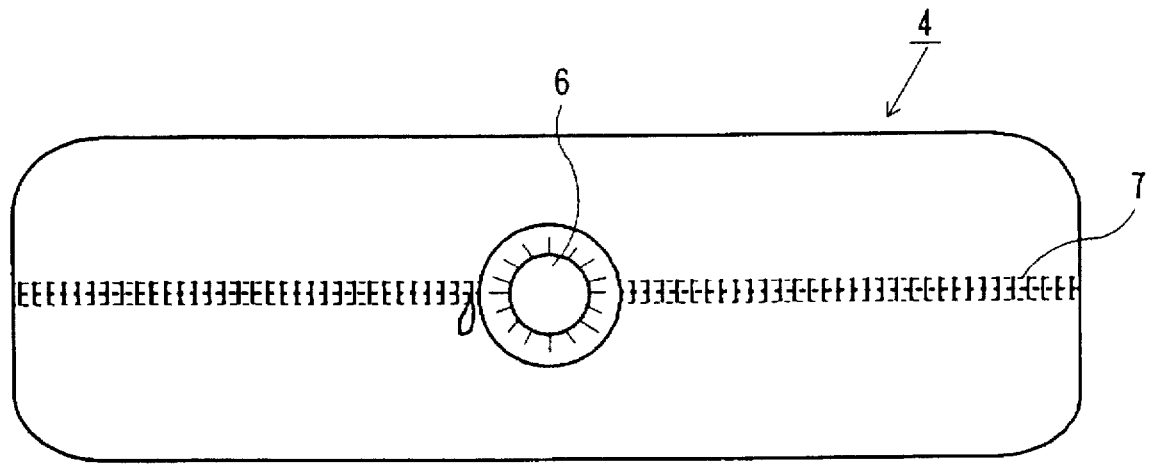
FIG. 3 is a diagram illustrating the arrangement of a cover for the second embodiment of the apparatus according to the first invention.
Figure 4:
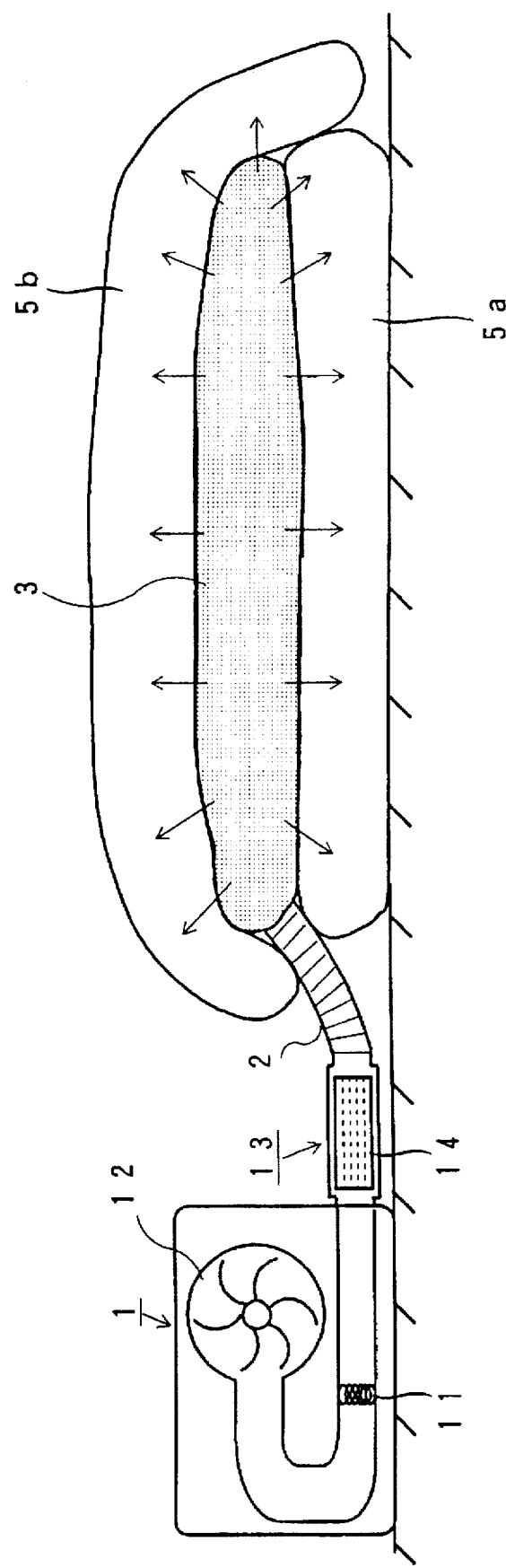
FIG. 4 is a diagram illustrating another arrangement of an alkaline chlorine dioxide gas generator according to the first invention.

FIGS. 1 through 4 are diagrams for explaining an apparatus according to the first invention. FIG. 1 is a diagram illustrating the arrangement of a first embodiment of an apparatus according to the first invention; FIG. 2 is a diagram illustrating the arrangement of a second embodiment of the first invention; FIG. 3 is a diagram for explaining the arrangement of a cover according to a second embodiment; and FIG. 4 is a diagram illustrating another arrangement for an alkaline chlorine dioxide gas generator according to the first invention.

Reference number 1 denotes a warm air generator; 2, a hose; 3, an air-permeable air mattress; 4, an air-permeable cover; 5a, a mattress; 5b, a coverlet; 10, a warm air nozzle; 11, a heater; 12, a fan; 13, an alkaline chlorine dioxide gas generator; and 14, a ceramic body that is impregnated with an alkaline chlorine dioxide solution.

As is shown, the warm air generator 1 includes the warm air nozzle 10, the heater 11 and the fan 12. An air stream that is driven by the fan 12 is heated by the heater 11 and is blown through the warm air nozzle 10.

The warm air that is blown through the nozzle 10 passes through the alkaline chlorine dioxide gas generator 13 and absorbs alkaline chlorine dioxide gas. The air containing the gas is transmitted through the hose 2 and is ejected through the surface of the air mattress 3. The warm air is blown against the mattress 5a and the coverlet 5b.

As is shown in FIG. 2, the air mattress 3, the mattress 5a and the coverlet 5b are covered by the air-permeable cover 4. Warm air that contains alkaline chlorine dioxide gas is ejected from the air mattress 3 and fills the cover 4. The warm air uniformly permeates all of the mattress 5a and the coverlet 5b, and deodorizes, sterilizes and dries them.

The warm air that contains the alkaline chlorine dioxide gas dioxide gas and that fills the cover 4 then overflows from the cover 4. The chlorine dioxide gas that is contained in the warm air cleans the immediate atmosphere by performing deodorization, but as the concentration of chlorine dioxide is 1000 ppm or less, the gas is harmless to humans.

The cover 4 is air permeable, so that the warm air that overflows from the cover 4 is discharged to the outside. As is shown in FIG. 3, the cover 4 also has a hose insertion port 6, into which the hose 2 is inserted, and a zipper 7, provided around it, that is opened and closed to permit the exchange of mattresses, pillows, etc.

Further, as is shown in FIG. 4, the alkaline chlorine dioxide gas generator 13 according to the present invention is detachably connected to the hose 2 outside the warm air generator 1.

Figure 5:
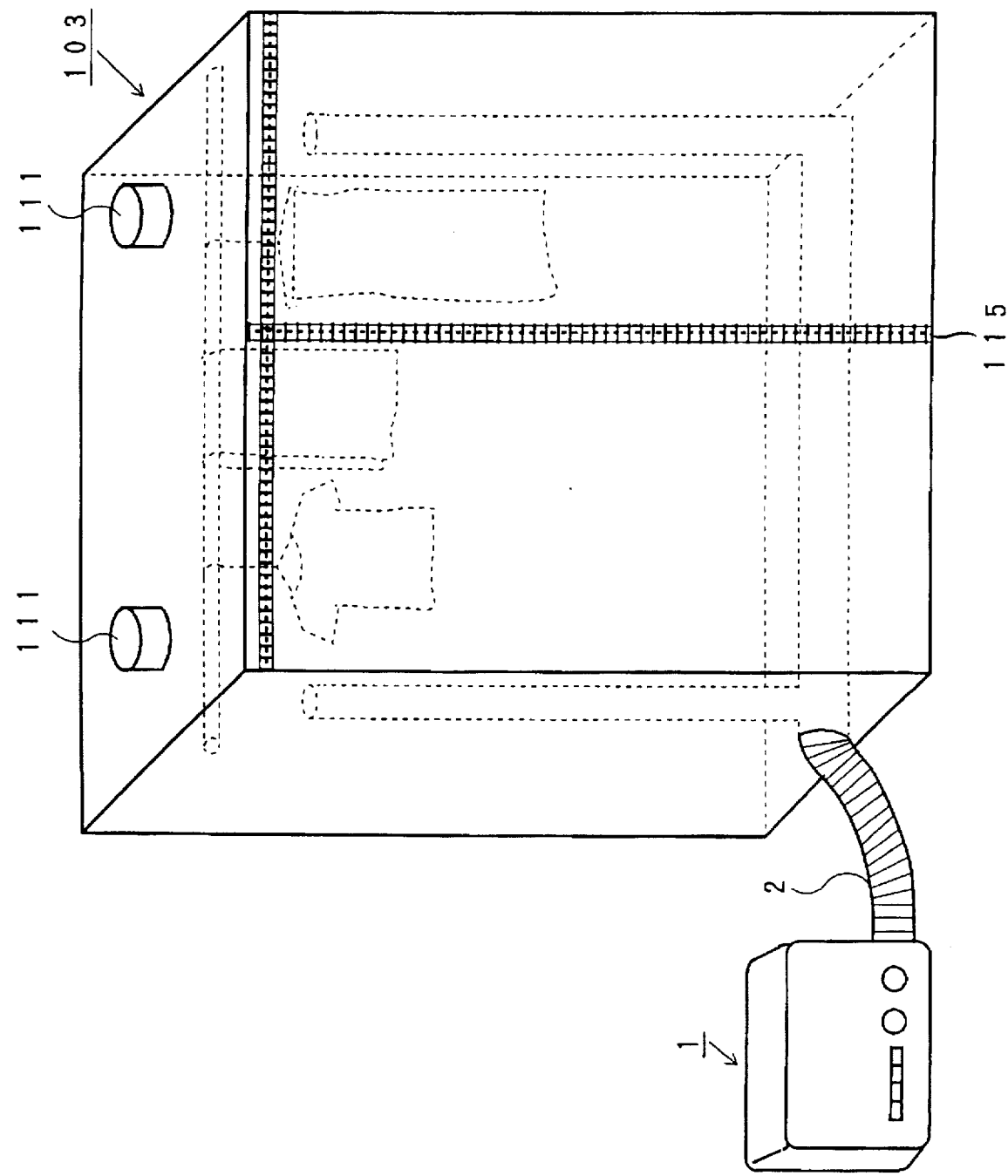
FIG. 5 is a diagram illustrating the general arrangement of an apparatus according to a second invention.
Figure 6:
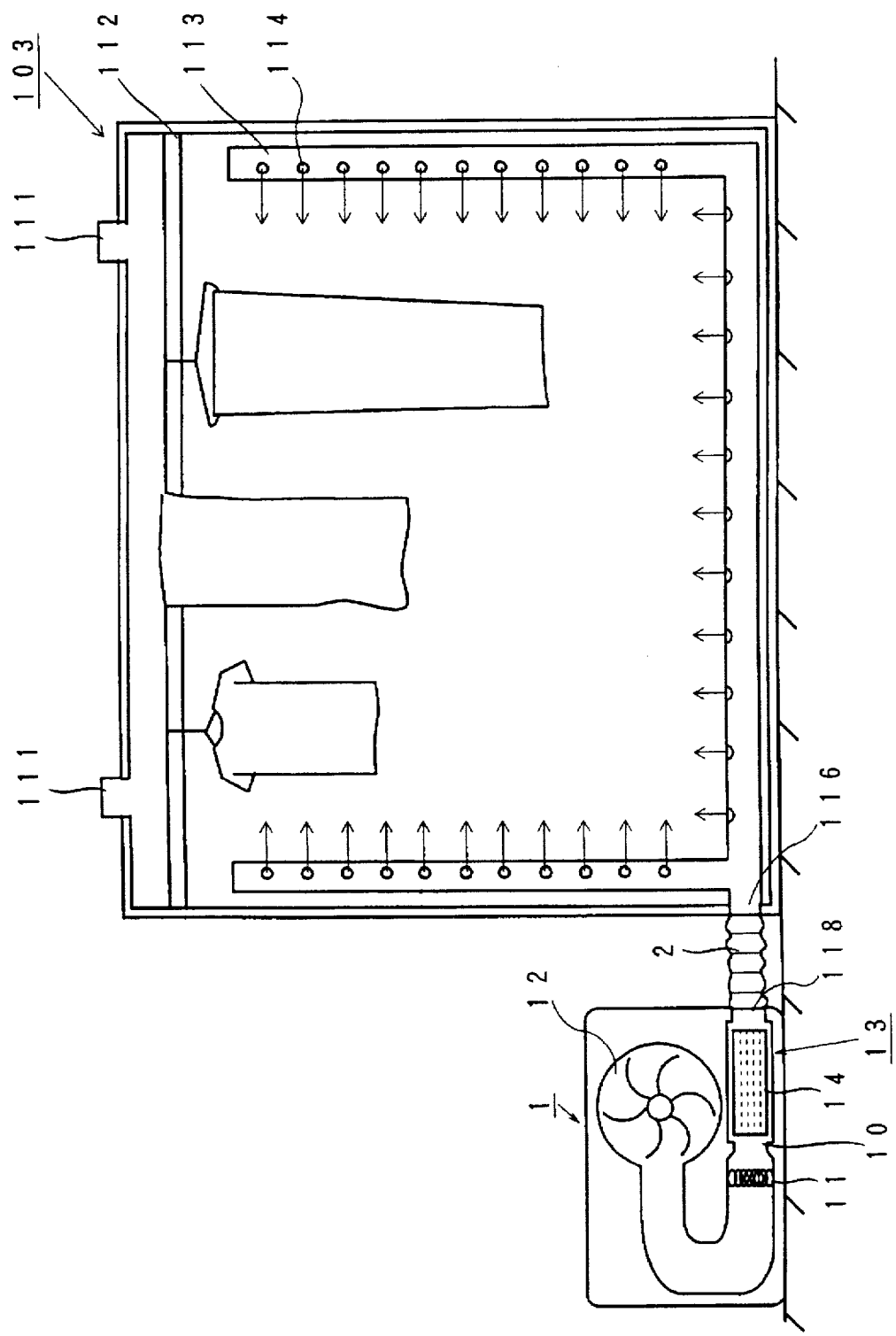
FIG. 6 is a diagram illustrating the arrangement of one embodiment of the apparatus according to the second invention.
Figure 7:
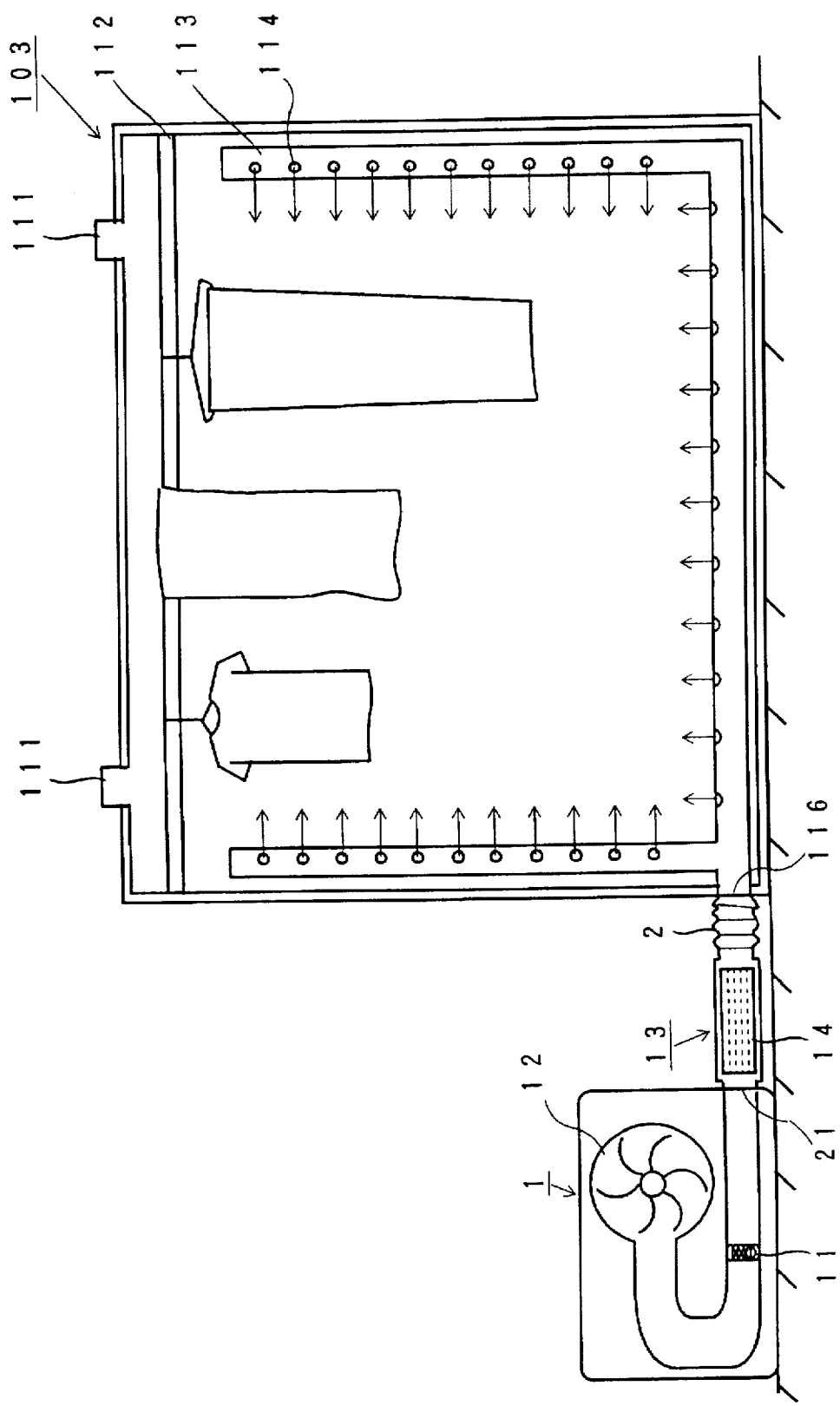
FIG. 7 is a diagram illustrating another arrangement of an alkaline chlorine dioxide gas generator according to the second invention.
Figure 8A:
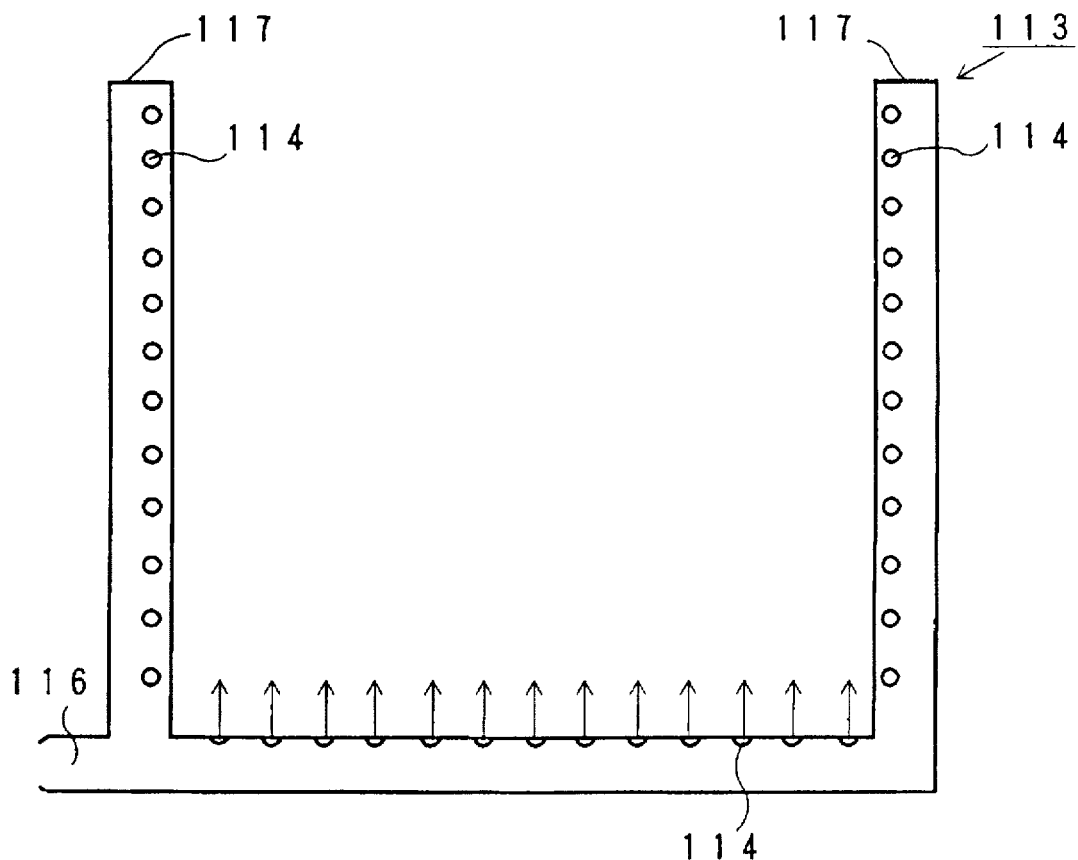
FIG. 8A is a front cross sectional view of a warm air pipe according to the second invention.
Figure 8B:
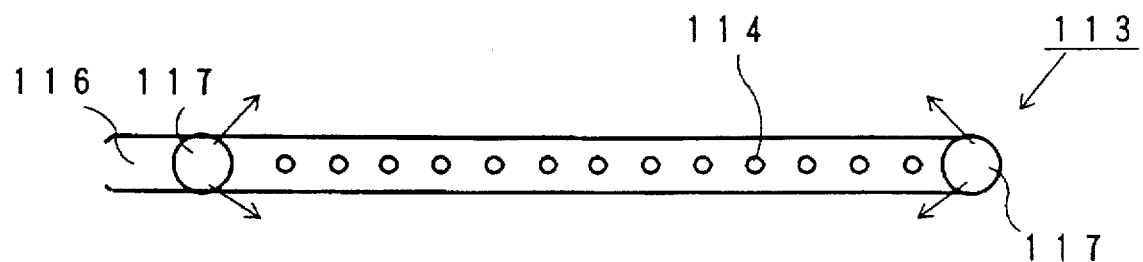
FIG. 8B is a plan cross sectional view of a warm air pipe according to the second invention.
Figure 9:
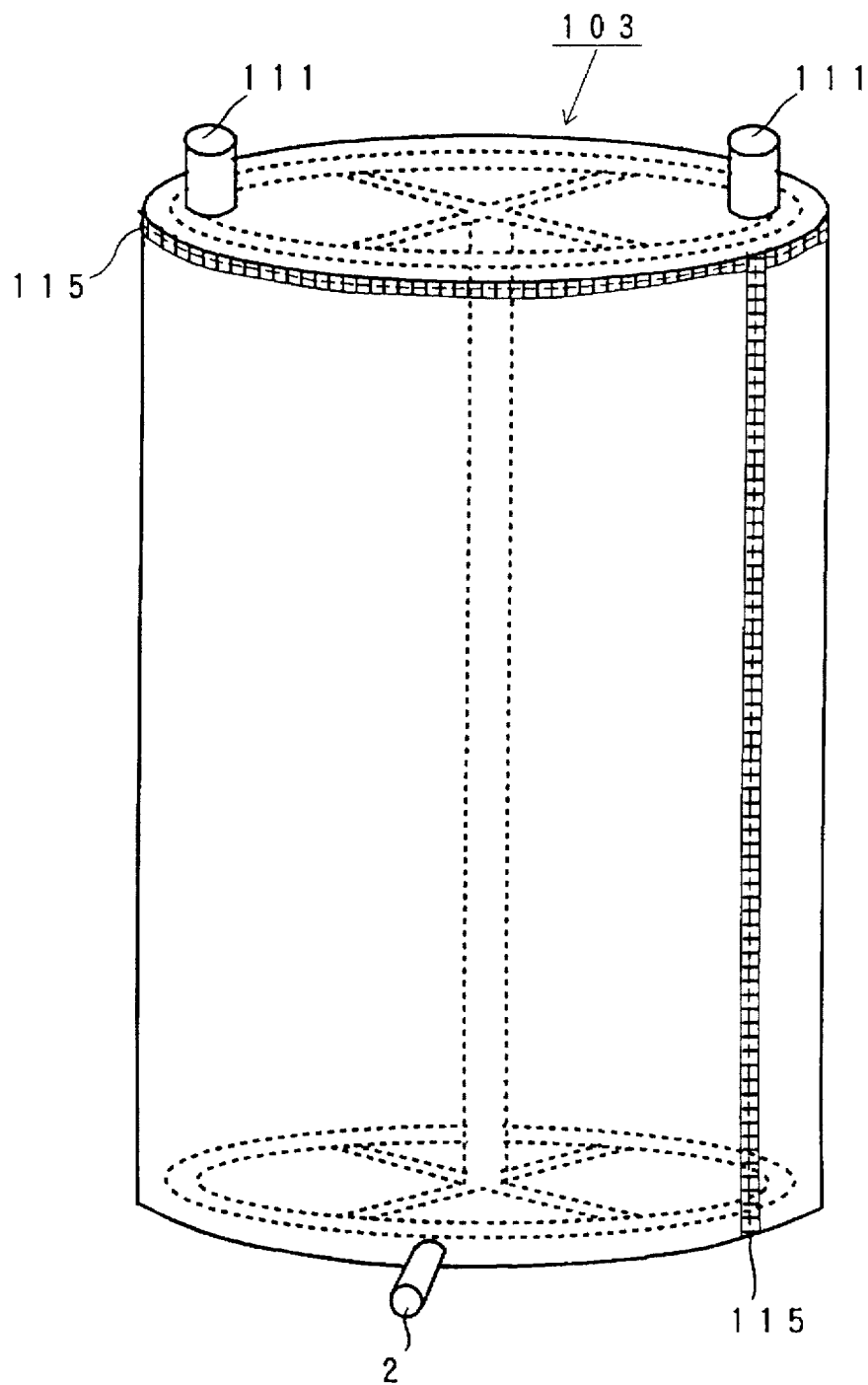
FIG. 9 is a diagram illustrating another arrangement of a deodorization, sterilization and drying case according to the second invention.

The preferred embodiment of a second invention will now be described while referring to FIGS. 5 through 9. FIG. 5 is an external diagram illustrating the general arrangement of an apparatus according to the second invention; FIG. 6 is a cross sectional view of the arrangement of a first embodiment of the apparatus according to the second invention;

FIG. 7 is a diagram illustrating another arrangement of an alkaline chlorine dioxide gas generator according to the second invention; FIG. 8A is a front cross sectional view of a warm air pipe according to the second invention, and FIG. 8B is its plan cross section; and FIG. 9 is a diagram illustrating another arrangement of a sterilization, deodorization and drying case according to the second invention.

A case 103 for drying clothing is employed wherein clothing, etc., which are the objects for which deodorization, sterilization and drying are performed, are retained while being deodorized, sterilized and dried. The drying case 103 includes air outlets 111, a rod 112 from which clothing, etc., are hung, and a warm air pipe 113, which has a coupling portion 116 by which it is connected with a hose 2, in which warm air ejection holes 114 are formed.

Zippers 115 are provided for the drying case 103. To load the clothing inside the case, the zippers 115 are unfastened, and when the apparatus is to be activated, the zippers 115 are fastened to close the case 103.

After the zippers 115 are unfastened, clothing to be processed is hung directly on the rod 112 in the case 103, or is arranged on hangers that are then hooked over the rod 112.

Air outlets 111 that are located on the top of the case 103 are used to discharge to the outside the alkaline chlorine dioxide gas that overflows from the drying case 103. The alkaline chlorine dioxide gas that is discharged from the air outlets 111 is harmless, and purifies the atmosphere.

Although the example wherein the two air outlets 111 are located on the top of the drying case 103 is shown, the locations and the number of outlets 111 are arbitrarily determined, depending on the size of the apparatus and the installation site.

FIG. 8A is a front cross section of the warm air pipe 113, and FIG. 8B is its plan cross view. Reference number 114 is used to denote the warm air ejection holes; 116, a coupling portion that is connected to the hose 2; and 117, the ends of the warm air pipe 113.

The coupling portion 116 that is connected to the hose 2 is open and receives warm air from a warm air generator 1. The other ends 117 of the warm air pipe 113 is closed. A plurality of warm air ejection holes 114 are formed so that they are directed upward in the horizontal portion of the warm air pipe 113, and are formed so that they are directed slightly inward in the right and left upright portions of the pipe 113. It is preferable that the diameter of the warm air ejection holes 114 be 0.2 to 0.7 mm.

Warm air that contains alkaline chlorine dioxide gas is driven through the warm air ejection holes 114, which are formed in the horizontal portion and upright portions of the warm air pipe 113, so that it fills the entire clothing drying case 103.

The warm air pipe 113 in which are formed the warm air ejection holes 114 is preferably a heat-resisting vinyl chloride pipe. Although one warm air pipe is provided in this embodiment, while taking the size of the apparatus into consideration, a plurality of such pipes may be used or the pipe may be located at the bottom of the drying case.

Although in FIG. 5 the zippers 115 are located vertically at the front center of the drying case 103 and horizontally along the upper edge, the zippers may be located vertically at the front center and horizontally along the upper and lower edges. The locations of the zippers are not, however, limited to those described here.

In addition, although the warm air pipe 113 is coupled with the hose 2, while taking the installation site of the apparatus into consideration, another arrangement can be employed, just so long as warm air from the warm air generator 1 can be transmitted to the warm air pipe 113. Further, the warm air pipe 113 may be directly connected to the warm air generator 1.

The warm air generator 1 comprises, at the least, a fan 12, a heater 11, and a warm air nozzle 10. As is shown in FIG. 6, in the warm air generator 1 an alkaline chlorine dioxide gas generator 13 can be detachably located between the warm air nozzle 10 and a coupling portion 118, which connects the warm air generator 1 to the hose 2. Further, as is shown in FIG. 7, the alkaline chlorine dioxide gas generator 13 may be a constructed as cartridge that is located outside the warm air generator 1 and that couples the warm air nozzle 10 of the warm air generator 1 with the hose 2.

A timer is provided for the warm air generator 1, and the timing for deodorization, sterilization, and drying by the apparatus can be selected in advance in consonance with the types and number of objects. Automatic processing of the objects is possible.

The hose 2 connects the warm air pipe 113, which is attached to the clothing drying case 103, with the warm air generator 1. The hose 2 is a medium by which warm air, which is driven from the warm air generator 1 through the alkaline chlorine dioxide gas generator 13, that contains alkaline chlorine dioxide gas is transmitted to the warm air pipe 113. The hose 2 is made of, for example, heat-resisting vinyl chloride and can be readily extended and compressed.

With this arrangement, an air stream that is driven by the fan 12 and heated by the heater 11 passes through the warm air nozzle 10 and the alkaline chlorine dioxide gas generator 13 and travels along the hose 2 to the warm air pipe 113. The air is then discharged from the warm air ejection holes 114 into the drying case 103. The warm, discharged air fills the drying case 103, and deodorizes, sterilizes and dries the clothing inside.

As is shown in FIG. 9, the clothing drying case 103 can be formed so that it is cylindrical, and a rod for hanging clothing, etc., can be formed so that it is circular. With this structure, since the drying case 103 is cylindrical, even when warm air that contains alkaline chlorine dioxide gas is introduced directly into the drying case 103 without using the warm air pipe 113, the warm air can smoothly fill the entire drying case 103.

Furthermore, with this arrangement the selection of sites where this device can be installed can be increased, and a more usable apparatus can be provided.

Figure 10:
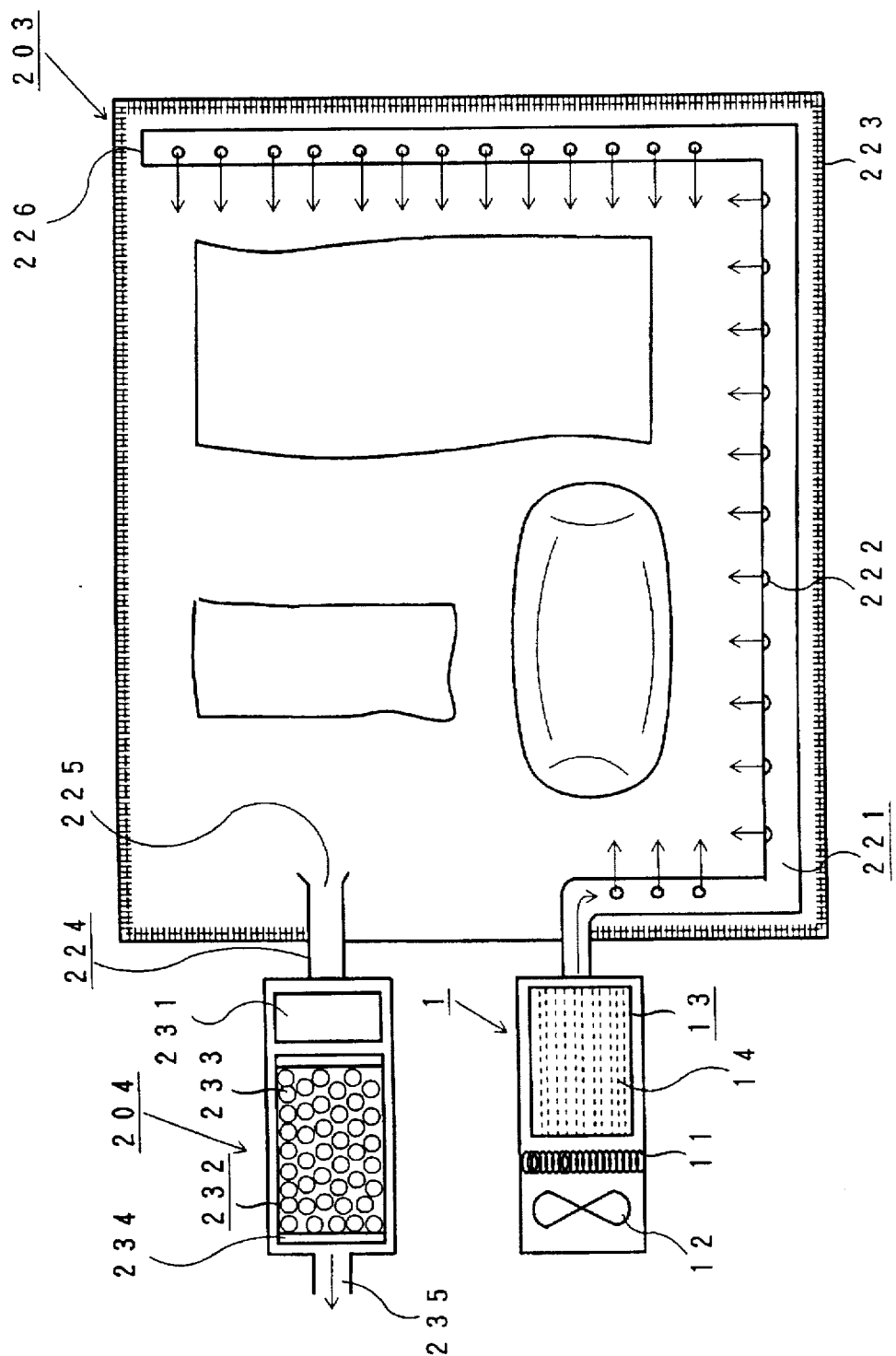
FIG. 10 is a diagram illustrating the general arrangement of an apparatus according to a third invention.
Figure 11:
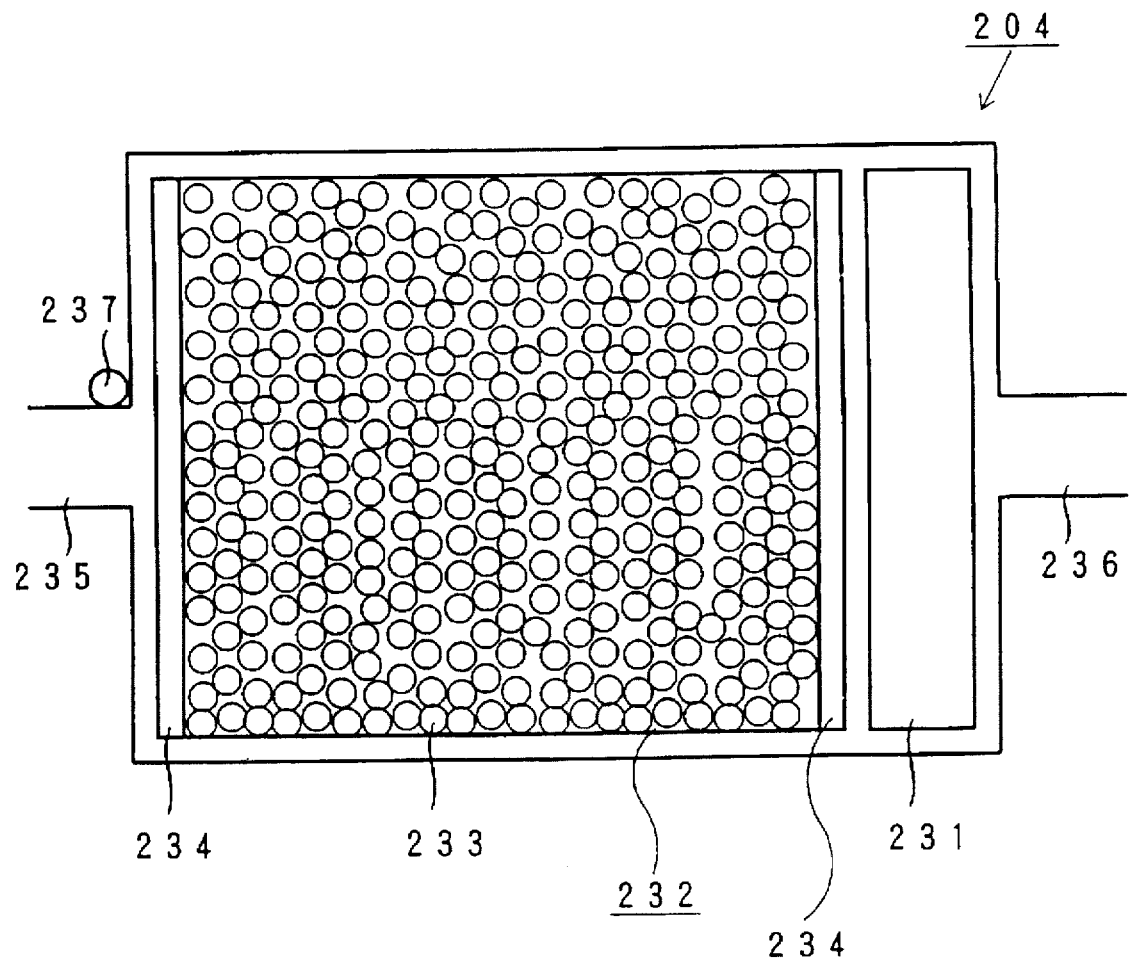
FIG. 11 is a diagram illustrating the arrangement of a warm air filter according to the third invention.

The preferred embodiment of a third invention will now be explained while referring to FIGS. 10 and 11. FIG. 10 is a diagram illustrating the general arrangement of an apparatus according to the present invention; and FIG. 11 is a cross sectional view of the structure of a warm air filter 204 according to the third invention.

As is shown in FIG. 10, an apparatus according to the third invention comprises: a warm air generator 1 for supplying heated air that contains alkaline chlorine dioxide gas; a bag 203 in which bedding is retained and deodorized, sterilized, and dried; and a warm air filter 204 for filtering warm air after it is used for deodorization, sterilization and drying, and for discharging the filtered air to the outside.

With the above described arrangement, when an air stream that is heated in the warm air generator 1 is brought into contact with and passes through a ceramic body 14 via through holes that are internally formed in the ceramic body 14, alkaline chlorine dioxide gas is generated and is mixed with the air stream.

The alkaline chlorine dioxide content of the impregnation solution that is used with the present invention is 500 ppm to 3000 ppm, when the content is calculated for chlorine dioxide, and is preferably 1000 ppm to 2500 ppm. The chlorine dioxide that is used with the apparatus of the present invention can be replaced with ozone.

The bag 203 according to the third invention will now be described. In the bag 203, bedclothes, etc., are retained and deodorized, sterilized and dried. The bag 203 has a warm air pipe 221 and a warm air absorption pipe 224, and can be opened and closed by a zipper 223 when objects to be processed are exchanged.

The bag 203 must be non-air-permeable in order for it to satisfactorily deodorize, sterilize and dry the bedclothes that are enclosed within it. In FIG. 10 is shown an example where the zipper 223 is located around the entire circumferential edge of the bag 203; however, the position of the zipper is not limited to the one that is illustrated, and the zipper may be provided vertically and horizontally at the center portion, or along the adjacent two sides of the bag.

The warm air, from the warm air generator 1, that contains alkaline chlorine dioxide gas is passed through the warm air pipe 221 that is used. One end of the warm air pipe 221 is detachably coupled with the warm air generator 1 by a coupling portion 219, and the other end 226 is closed. Multiple warm ejection holes 222 are formed longitudinally and inwardly along one part of the circumference of the pipe 221, so that the warm air is discharged through the holes 222 into the bag 203.

Although in FIG. 10 the warm air pipe 221 is positioned along three sides of the bag 203, the location of the pipe 221 is not thus limited, and the pipe 221 may be installed along all the sides of the bag 203.

The warm air that is used for deodorizing, sterilizing and drying bedclothes is passed through the warm air absorption pipe 224 that is employed and is forwarded to the warm air filter 204. One end of the absorption pipe 224 is detachably coupled with the warm air filter 204 by a coupling portion 236, and the other end is open and forms a warm air absorption nozzle 225.

The warm air pipe 221 and the warm air absorption pipe 224 are preferably made of heat-resisting vinyl chloride. The warm air pipe 221 can communicate with the warm air generator 1 via a hose at the coupling portion 219, and the warm air absorption 224 can communicate with the warm air filter 204 by a hose at the coupling portion 236.

The alkaline chlorine dioxide gas generator 13 according to the third invention, as well those setups according to the first and the second inventions, can be detachably connected to a hose outside the warm air generator 1.

With this arrangement, the zipper 223 is unfastened and mattresses and bed sheets that are used in hospitals, etc., are placed in the bag 203. Then, the zipper 223 is fastened to securely close the bag 203. The warm air generator 1 is activated and generates warm air that contains alkaline chlorine dioxide gas. The warm air is transmitted to the warm air pipe 221, and is discharged through the multiple warm air ejection holes 222 and fills the bag 203.

The bedclothes in the bag 203 are completely deodorized, sterilized and dried by the warm air that contains alkaline chlorine dioxide gas; and after the process is over, the air enters the warm air absorption nozzle 225 and passes through the warm air absorption pipe 224 to the warm air filter 204.

As the air that is introduced into the bag 203 contains alkaline chlorine dioxide gas, it deodorizes and sterilizes mattresses, etc., in the bag; and as the air is warm and alkaline, it sterilizes the objects and also accelerates drying and prevents molds. By utilizing the obtained synergistic effect, the apparatus of the present invention ensures that objects will be deodorized and sterilized, and also dried.

The arrangement of the warm air filter 204 according to the present invention will now be explained while referring to FIG. 11.

The warm air filter 204 filters warm air that is received through the warm air absorption pipe 224 after the air has been used for the deodorization, sterilization and drying process, and discharges the filtered air from air outlet 235.

As is shown in FIG. 11, in the warm air filter 204, a filter medium 231 is located on the side of the portion 236 that is coupled with the warm air absorption pipe 224, and an adjusting filter medium 232 is provided on the side of the warm air outlet 235, from which air is discharged to the outside.

Since the filter medium 231 and the adjusting filter medium 232 have to be exchanged when they have been used for a predetermined time, the filter media 231 and 232 are detachable from the warm air filter 204 so that they can be replaced.

The filter medium 231 filters out dead ticks, dust, etc., which are contained in the warm air after it has been used for the deodorization, sterilization and drying process. Although a non-woven fabric or activated carbon is preferable for the filter medium 231, air-permeable woven cloth may be used so long as it can remove minute particles.

The adjusting filter medium 232 adjusts the warm air that is filtrated by the filter medium 231 so that it has a neutral pH value of pH 6 or pH 7. In the adjusting filter medium 232 are ceramic particles 233 that are packed in a container. Both ends of the container are sealed with non-woven fabrics 234.

Since the ceramic particles 233 in this embodiment are porous, the processing speed is high, and after the warm air has been used for the deodorization, sterilization and drying process it can be adjusted instantaneously to a neutral pH value of pH 6 or pH 7. The warm air that is thus adjusted and discharged from the air outlet 235 is harmless.

A pH sensor 237 can be provided in the vicinity of the air outlet 235. Then, if the pH sensor 237 detects warm air that is discharged from the air outlet 235 that has a pH level that exceeds the neutral, a notification to that effect can be made by, for example, an alarm that is connected to the pH sensor 237, and the adjusting filter medium 232 can be changed. In this manner, the warm air that is discharged to the outside will continually be maintained at a neutral level.

Therefore, the apparatus according to the present invention is harmless to a patient, even when it is installed near the patient's bed and is activated to perform the deodorization, sterilization and drying of the bed sheets, mattress, and clothing that the patient uses. The sites at which the apparatus can be installed are not limited, and the apparatus can be easily used anywhere and anytime.

In this embodiment, the warm air generator 1 and the warm air filter 204 are separately located. However, the warm air generator 1 and the warm air filter 204 can be stacked or arranged side by side as a single unit. This arrangement saves installation space and easy to carry.

According to the present invention, warm air for deodorization and sterilization can be surely and easily provided. The warm air ensures that bedclothes that are used in medical institutions can be deodorized, that sterilization to destroy disease germs can be performed, and that bedclothes can be dried. Further, since the warm air that is discharged to the outside of the apparatus of the invention is harmless, the apparatus can be installed in a patient's room and can easily be used to deodorize, sterilize and dry bedding, such as a mattress that is used in a medical institution, and the patient's clothing.

The structure of the alkaline chlorine dioxide gas generator 13, the provision of a timer for the warm air generator 1, the structure of a ceramic body that is internally provided in the alkaline chlorine dioxide gas generator 13, and the structure of a solution supply device 15 for supplying alkaline chlorine dioxide solution are the same as those for the first invention.

According to the first through the third inventions with the described structure, when warm air that is blown through the warm air nozzle 10 passes through the alkaline chlorine dioxide gas generator 13, the air contacts the ceramic body 14 that is internally provided in the alkaline chlorine dioxide gas generator 13 and that is impregnated with an alkaline chlorine dioxide solution.

By this contact, alkaline chlorine dioxide gas is generated, and the warm air is mixed with the alkaline chlorine dioxide gas. The warm air containing the contains alkaline chlorine dioxide gas is transmitted through the hose 2, the warm air pipe 113 and the warm air pipe 221, and is ejected through the air mattress 3, the warm air ejection holes 114, and the warm air ejection holes 222. The warm air is blown directly against the bedclothes, or the bedding and clothing that are retained in the deodorization, sterilization and drying case 103 or the deodorization, sterilization and drying bag 203.

Taking into consideration the generation of alkaline chlorine dioxide gas and its drying effect on bedding, the temperature of the warm air should be from 40° C. to 70° C., preferably from 50° C. to 60° C.

The alkaline ceramic body reacts easily with heat. When air that is heated by endothermic reaction or heat release contacts a ceramic body that has been impregnated with an alkaline chlorine dioxide solution, alkaline chlorine dioxide gas is generated together with an alkaline gas that is released by the ceramic body.

Air that is heated to 50° C. to 60° C. kills ticks and dries bedding and clothing. Alkaline gas accelerates the drying and provides a sterilization effect. Gas that contains chlorine dioxide has a strong deodorization and sterilization effect.

Warm air that contains alkaline chlorine dioxide gas, which is generated by the alkaline chlorine dioxide gas generator 13, and is ejected though the air mattress 3 and the warm air ejection holes 114 and 222 can not only deodorize and sterilize bedding and clothing, but can also dry them at the same time.

As is shown in FIGS. 1 and 6, the alkaline chlorine dioxide gas generator 13 is detachably provided between the warm air nozzle 10 of the warm air generator 1 and the portion that couples together the warm air generator 1 and the hose 2.

With this structure, the alkaline chlorine dioxide gas generator 13 can be constructed as a cartridge, and the ceramic body 14 can be easily exchanged when a predetermined time has elapsed, so that the deodorization, sterilization and drying effects can be maintained. The apparatus of the present invention is simplified and is easy to store.

As is shown in FIGS. 4 and 7, the alkaline chlorine dioxide gas generator 13 can be located as a cartridge outside the warm air generator 1, for example, at the coupling portion for the warm air generator 1 and the hose 2. With this arrangement, the replacement of the ceramic body 14 is easy.

A timer is provided for the warm air generator 1, and the timing for deodorization, sterilization and drying by the apparatus can be set in advance, in consonance with the types and number of objects, and automatic processing of the objects is possible.

Figure 12:
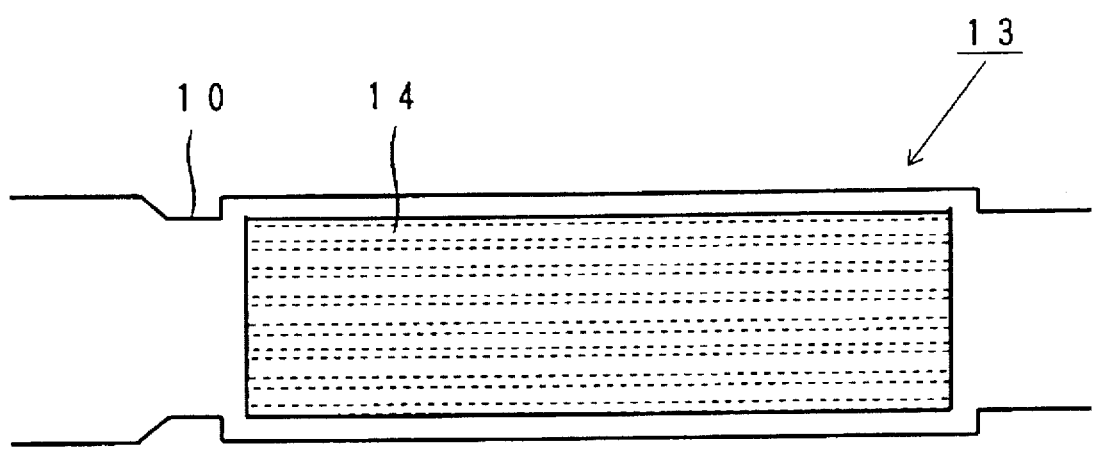
FIG. 12 is a diagram illustrating the arrangement of an alkaline chlorine dioxide gas generator according to the first through third inventions.
Figure 13:
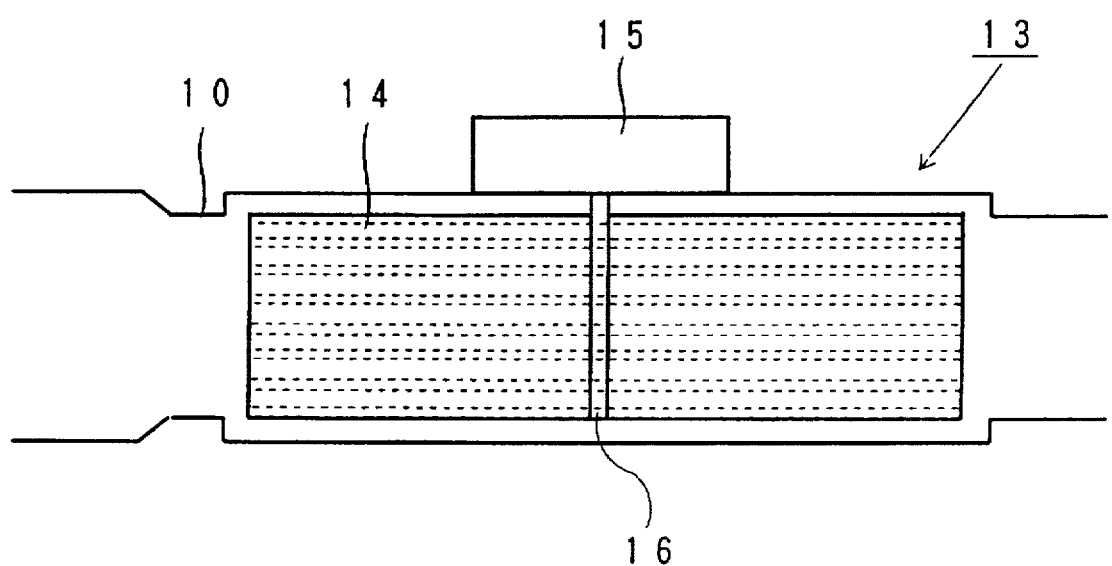
FIG. 13 is a diagram illustrating another arrangement of an alkaline chlorine dioxide gas generator according to the first through third inventions.

FIG. 12 is a cross sectional view of one example arrangement of the alkaline chlorine dioxide gas generator 13. FIG. 13 is a cross sectional view of another example arrangement of the alkaline chlorine dioxide gas generator 13. As is shown, the ceramic body 14 that has been impregnated with an alkaline chlorine dioxide solution is provided in the alkaline chlorine dioxide gas generator 13.

The ceramic body 14 that is provided in the alkaline chlorine dioxide gas generator 13 is impregnated with an alkaline chlorine dioxide solution. When the alkaline chlorine dioxide solution content of the ceramic body 14 is reduced, it must be replaced by a new ceramic body that has been impregnated with the named solution.

With the arrangement shown in FIG. 12, the structure of the alkaline chlorine dioxide gas generator 13 is simplified and the apparatus of the invention has also a simple structure. The alkaline chlorine dioxide solution content is limited, and thus the ceramic body 14 must be replaced frequently.

As is shown in FIG. 13, a solution supply groove 16, along which an alkaline chlorine dioxide solution is supplied, is formed in the ceramic body 14, which is located in the alkaline chlorine dioxide gas generator 13. A solution supply unit 15 is detachably mounted on the alkaline chlorine dioxide gas generator 13, so that an alkaline chlorine dioxide solution can be supplied along the solution supply groove 16 to the ceramic body 14.

According to the arrangement shown in FIG. 13, although the structure of the alkaline chlorine dioxide gas generator 13 is complicated, as an alkaline chlorine dioxide solution is fed to the ceramic body 14 from the solution supply unit 15, the length of the period before the ceramic body 14 must be replaced can be extended, and the deodorization and sterilization effects can be increased.

Further, since the chlorine dioxide solution supply unit 15 is detachably mounted on the alkaline chlorine dioxide gas generator 13, supplementation of the alkaline chlorine dioxide solution for the solution supply unit 15 can be facilitated.

An alkaline chlorine dioxide solution is fed from the solution supply unit 15 along the solution supply groove 16, which is formed in the ceramic body 14, and completely permeates the ceramic body 14 via through holes 17 and 18, which are formed in the ceramic body 14.

The ceramic body 14, which has multiple micropores, absorbs a solution well due to capillary action, and permits the solution to permeate it easily. In addition, when warm air contacts such a ceramic body, the generation of chlorine dioxide gas is accelerated.

Figure 14A:
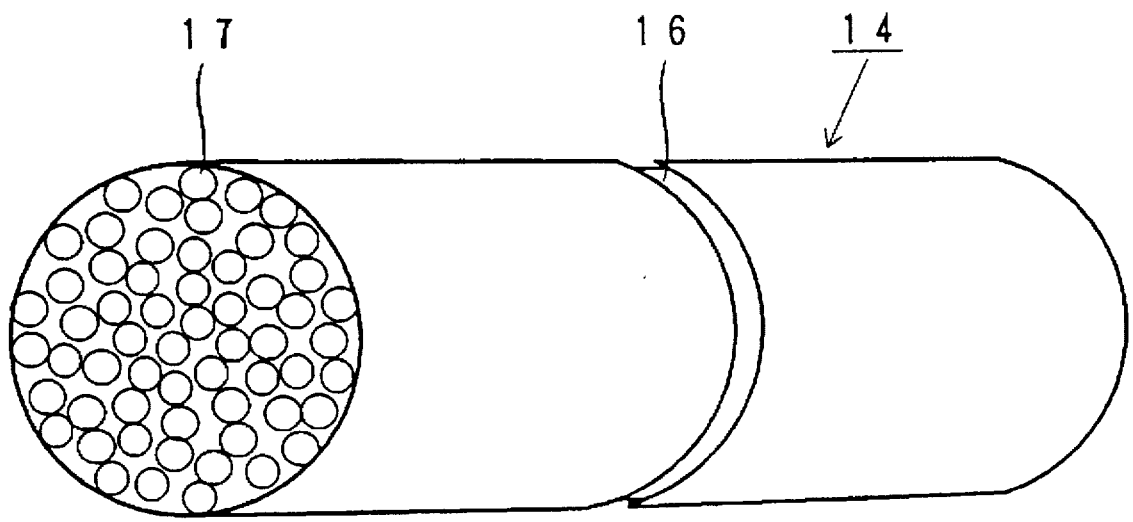
FIGS. 14A and 14B are external diagrams showing an example arrangement of a ceramic body according to the inventions, with FIG. 14A in particular showing an example in which a solution supply groove is formed.
Figure 14B:
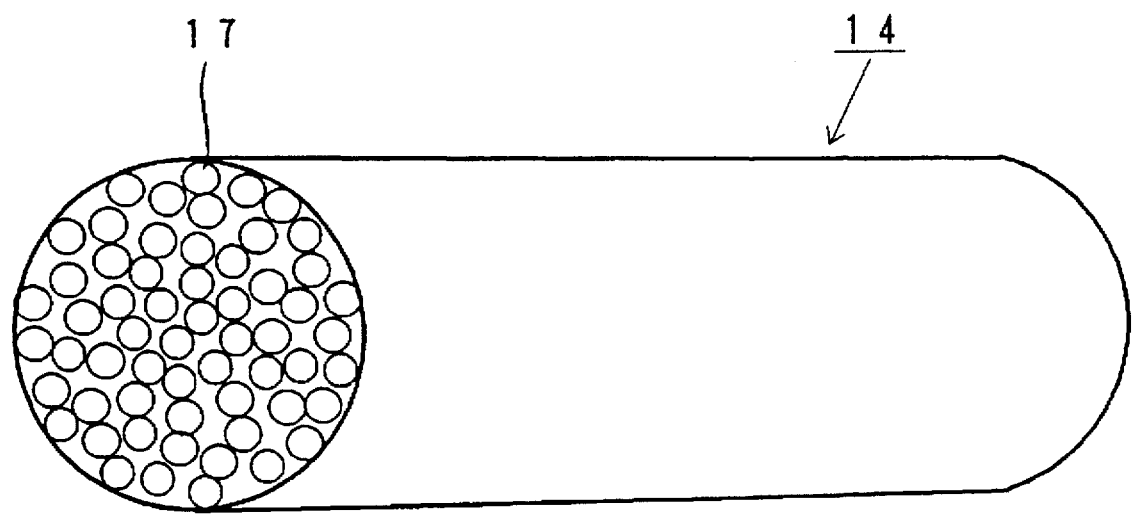
Figure 15A:
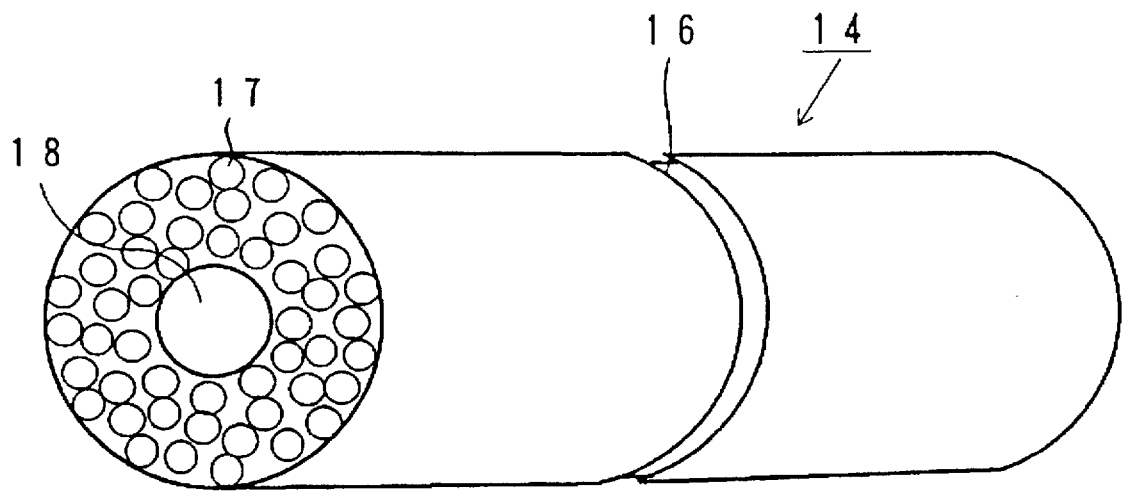
FIGS. 15A and 15B are diagrams showing another example arrangement of a ceramic body according to the inventions, with FIG. 15A in particular showing an example in which a solution supply groove is formed.
Figure 15B:
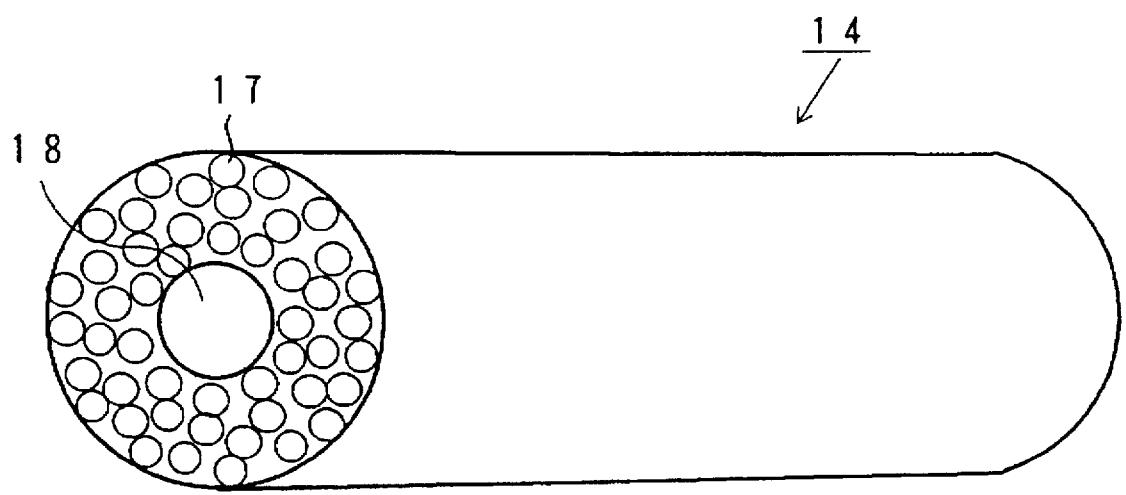

FIGS. 14A and 14B are diagrams illustrating examples of the ceramic body 14, and FIGS. 15A and 15B are diagrams illustrating other examples of the ceramic body 14.

In both FIGS. 14A and 15A are shown the ceramic body 14 wherein is formed the solution supply groove 16, along which an alkaline chlorine dioxide solution is supplied by the solution supply unit 15.

As is shown in FIGS. 14 and 15, the ceramic body 14 is columnar, cylindrical, for example, and a plurality of the through holes 17 are provided in its cross section in the longitudinal direction. It is desirable that multiple through holes 17 be formed for good ventilation.

As is shown in FIG. 14, when many of the comparatively small through holes 17 that have an identical diameter are formed longitudinally in the ceramic body 14, after warm air has passed through the through holes 17, the ceramic body 14 contains more alkaline chlorine dioxide gas, and the deodorizing and sterilizing effects are accordingly increased.

As is shown in FIG. 15, a through hole 18 having a large diameter is also provided in the center of the cross section of the ceramic body 14, and many through holes 17 having a smaller diameter are arranged around the large through hole 18.

With this arrangement, the backflow to the heater 11 of an air stream that contains alkaline chlorine dioxide gas can be prevented.

The air that is heated by the heater 11 passes through the through holes 17 and 18 in the ceramic body 14, while contacting the ceramic body 14 that is impregnated with an alkaline chlorine dioxide solution. Then, warm air that is mixed with alkaline chlorine dioxide gas is transmitted via the hose 2 and the warm air ejection holes 114 and 222 to the air mattress 3, the deodorization, sterilization and drying case 103 or the deodorization, sterilization and drying bag 203.

Chlorine dioxide is normally produced by an acid that acts on sodium chlorate or on calcium chlorate acid. Since the chlorine dioxide that is thus obtained is very explosive and dangerous, it must be handled very carefully.

Therefore, chlorine dioxide gas that has been stabilized in alkaline water, and that is thereafter kept in the stabilized state, has been developed (the gas is hereinafter referred to as "stabilized chlorine dioxide gas". It is well known that chlorine dioxide gas is excellent for deodorization and sterilization.

According to this invention, a ceramic body is immersed in the stabilized chlorine dioxide solution to obtain a ceramic body that is impregnated with the stabilized chlorine dioxide solution.

The pH value of the alkaline stabilized chlorine dioxide solution of the present invention is preferably pH 8 to pH 9.6. If the pH value is lower than 8 or higher than 9.6, the liberation of chlorine dioxide gas tends to be difficult, and the amount of chlorine dioxide gas that is contained in the heated air stream tends to be decreased.

Taking into consideration the fact that the objects to be processed are clothing and bedding that directly contact humans' bodies, and in order to reduce the adverse effect on humans as much as possible, for impregnation, the alkaline chlorine dioxide content of a solution for the first and the second inventions is 50 ppm to 1000 ppm, when the content is calculated for chlorine dioxide, and is preferably 100 ppm to 800 ppm. If the concentration of chlorine dioxide is less than 50 ppm, the deodorizing and sterilizing effects are reduced. The chlorine dioxide that is used by the apparatus of the present invention can be replaced with ozone.

On the other hand, taking into consideration the fact that the objects to be processed are clothing and bedding that are used in medical institutions, and that the processing is performed to kill disease germs, for impregnation, the alkaline chlorine dioxide content of a solution for the third invention is 500 ppm to 3000 ppm, when the content is calculated for chlorine dioxide, and is preferably 1000 ppm to 2500 ppm.

When air that is driven by the fan 12 and is heated by the heater 11 passes through the ceramic body 14 that is impregnated with a stabilized chlorine dioxide solution, the generation of chlorine dioxide gas is accelerated, and the amount of the chlorine dioxide gas in the warm air can be increased.

Such warm air is directed against the objects, such as bedclothes and clothing, and the objects can be deodorized and sterilized. Since the warm air is alkaline, drying of the objects can be accelerated and mold can be prevented.

The ceramic body 14 that is used in this invention absorbs an alkaline chlorine dioxide solution well, and generates chlorine dioxide gas that is mixed with warm air when the warm air from the fan contacts it and passes though.

The ceramic used in the present invention is an alkaline ceramic, and preferably contains at least one material selected from a group consisting of animal bone powder, shell powder, limestone powder, and coral powder.

In addition, the alkaline ceramic contains at least one ceramic selected from a group consisting of silica, alumina and zeolite.

Taking the absorption capability of an alkaline solution into account, a ceramic that contains powdered animal bones is desirable; moreover, when taking absorption speed into account, a ceramic wherein the proportion of powdered animal bones is high, for example, 50 to 80 weight %, is more desirable.

The powdered animal bones can be replaced with another alkaline adsorbent that has a high alkaline solution absorption capability.

An additional agent, such as a binder or a filling agent, is added to these ceramics, as necessary, to form a ceramic body 14 for the present invention.

The powdered animal bones described above are mainly those that are acquired by processing crude bones, especially the bones of cows, horses and sheep, that are commonly disposed of on farms, etc.

The crude bones are cut into an appropriate size for a calcination process, boiled, and calcined at around 900° C. to 1100° C. Since oxidized putrefaction occurs on bones if organic substances, such as gelatin, fat, protein and glue, that are not components of bone remain, such substances must be completely eliminated. During the boiling process, most organic substances that are attached not only to the external walls of bones but also inside pores along the surface of bones can be removed.

When the calcination process is then performed, the remaining organic substances can be removed completely, and simultaneously the humidity (water content) of the bone can be reduced to several percent or less, preferably to almost 0%.

Dependent on the calcining conditions, the bone is dried and maintains its original organization, which includes multiple fine pores. After the bone is cooled, it is crushed and then pulverized, and is formed into a bone powder having a size of about 20 to 200 mesh, more preferably 50 to 100 mesh, by a powdering machine.

The powdered bone has a yield of about 40 weight % of the original crude bone. The composition of the particles includes calcium (about 33 weight %) as a main component, phosphorus (about 16.7 weight %), barium (about 1.03 weight %), sodium (about 0.76 weight %), sulfur (about 0.64 weight %), and some magnesium, potassium, chlorine, amine, iron, and others. Multiple micropores communicate with each other both on the internal and external sides of the particles, which are alkaline.

Bentonite, Japanese acid clay, activated clay, kaolin clay, sericite, pyrophyllite, refractory clay, montmorillonite, or the like may be employed as a binder.

In this invention, the ceramic body 14 can be formed arbitrarily, as a particulate, or as a spherical or a columnar body, so long as the ceramic body 14 can be impregnated with an alkaline chlorine dioxide solution. But taking into consideration the impregnation by the alkaline chlorine dioxide solution, the discharge of chlorine dioxide gas, and the convenience of the device design, a columnar ceramic body 14 is preferable.

In the above embodiments, only the ceramic body 14 that is impregnated with an alkaline chlorine dioxide solution is provided in the chlorine dioxide gas generator 13. A ceramic body 14 that is impregnated with a citric acid solution can be provided on the side of the heater 11.

According to this arrangement, the generation of chlorine dioxide gas can be accelerated and the alkaline chlorine dioxide gas content of warm air can be increased, and thus the deodorization, sterilization and drying effects on bedding and clothing can be enhanced.

According to the present invention, warm air for deodorization and sterilization can be surely and easily supplied, and the deodorization, sterilization and drying of bedding and clothing can be ensured.

Experiment I

A mixture that consisted of 60 weight % of 100-mesh powdered cow bone, 20 weight % of silica, and 20 weight % of alumina, were formed into a spherical ceramic body having a diameter of about 18 mm.

The thus obtained ceramic body was heated to about 80° C. The resultant ceramic body was immersed in an alkaline chlorine dioxide solution at normal temperature for 10 to 60 seconds, and was then extracted to acquire a ceramic body that was impregnated with the alkaline chlorine dioxide solution. As is shown in FIG. 16B, a device model was built in which the thus obtained ceramic body, which was impregnated with the alkaline chlorine dioxide solution, was located adjacent to a dryer, and the nozzle of the dryer was connected to a vinyl bag, in the top of which a plurality of small holes were formed so that the gas from the dryer could be ejected into an acrylic box.

Figure 16A:
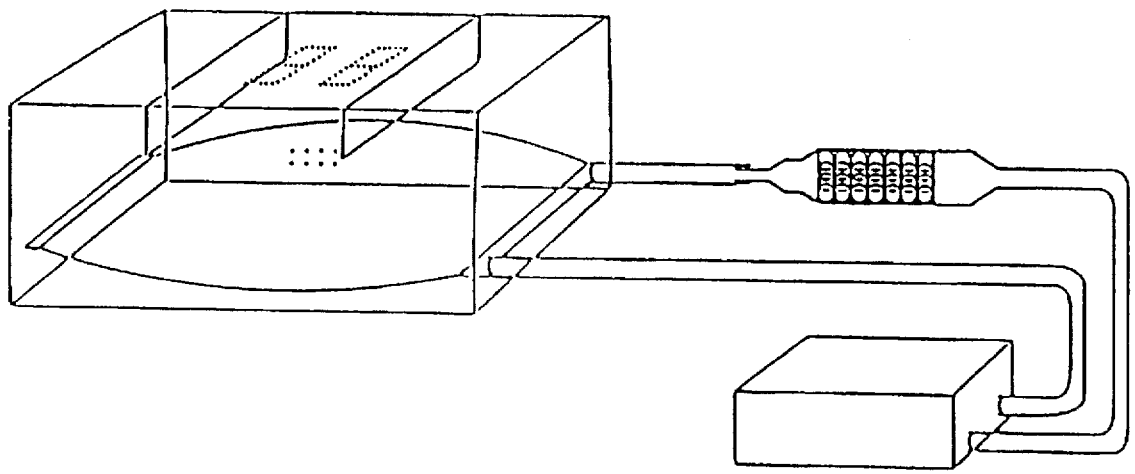
FIGS. 16A and 16B are diagrams showing device models according to the present invention that were produced for the sterilization effect experiments and for the measurement of the remaining amount of chlorine dioxide.
Figure 16B:
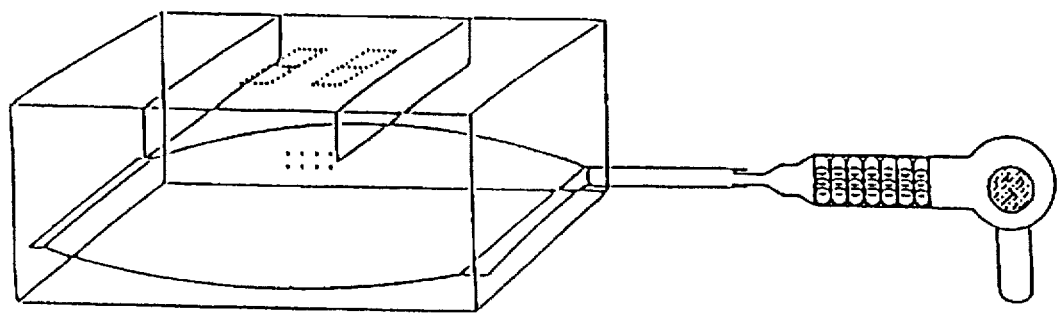
Figure 19:
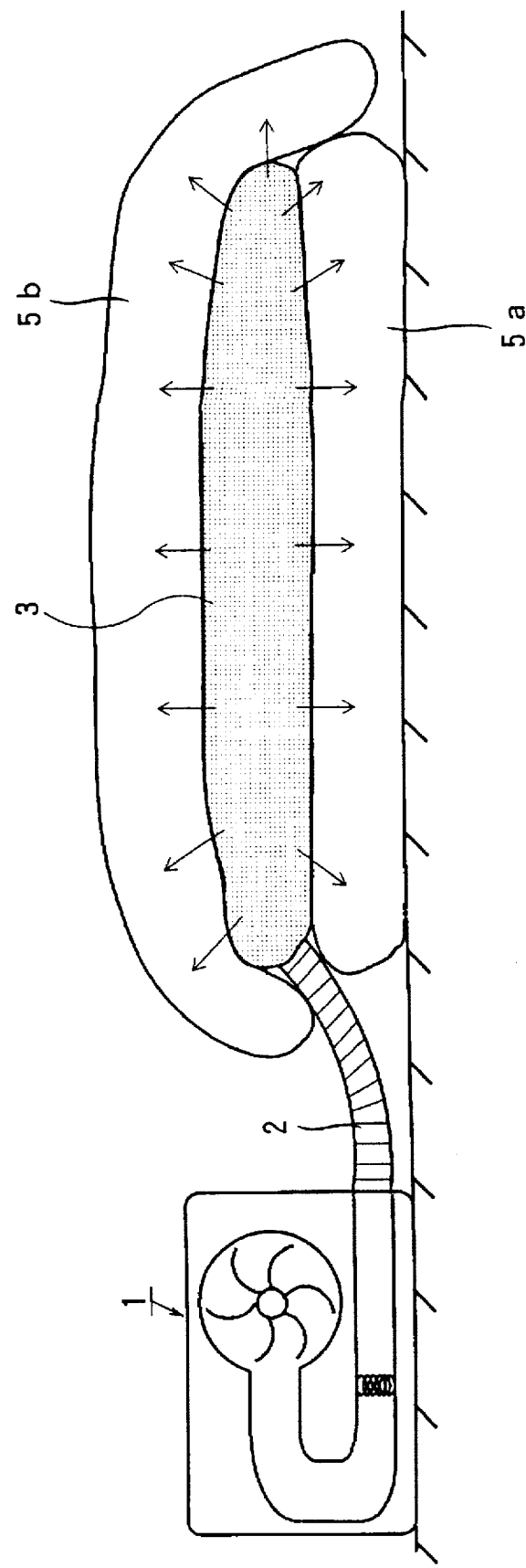
FIG. 19 is a diagram illustrating one example arrangement of a conventional bedding dryer.
Figure 20:
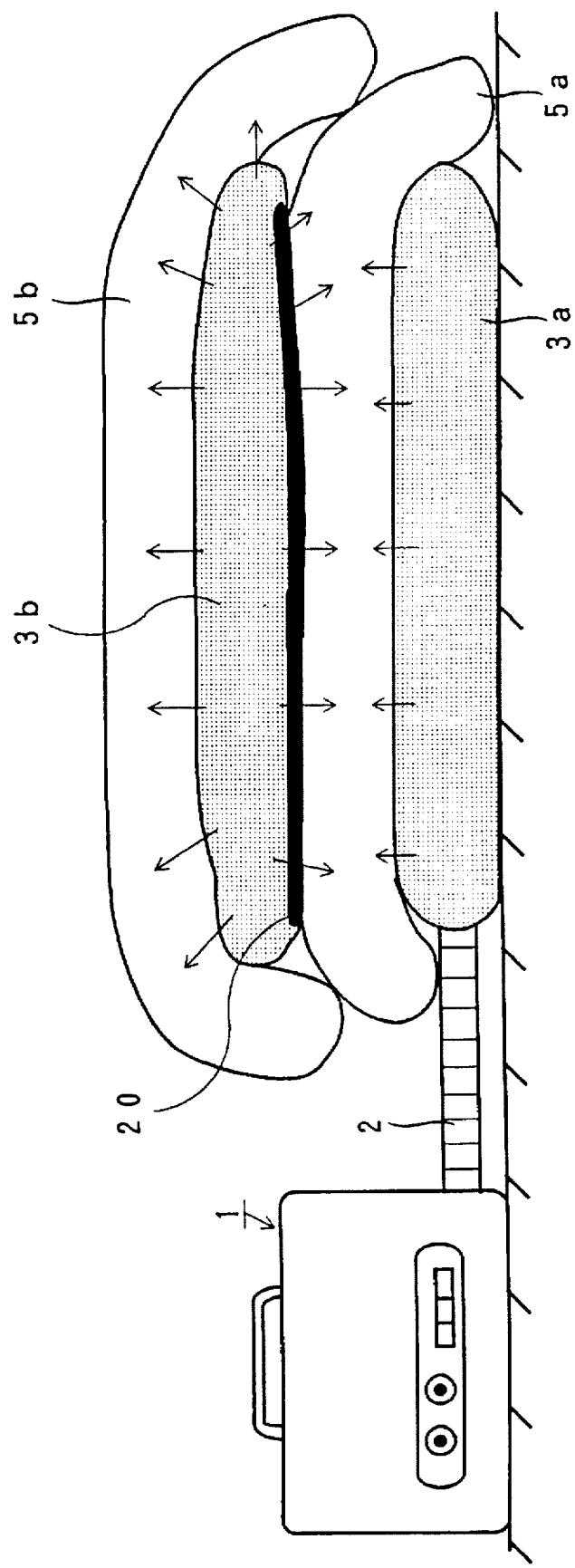
FIG. 20 is a diagram illustrating another example arrangement of a conventional bedding dryer.
Figure 21:
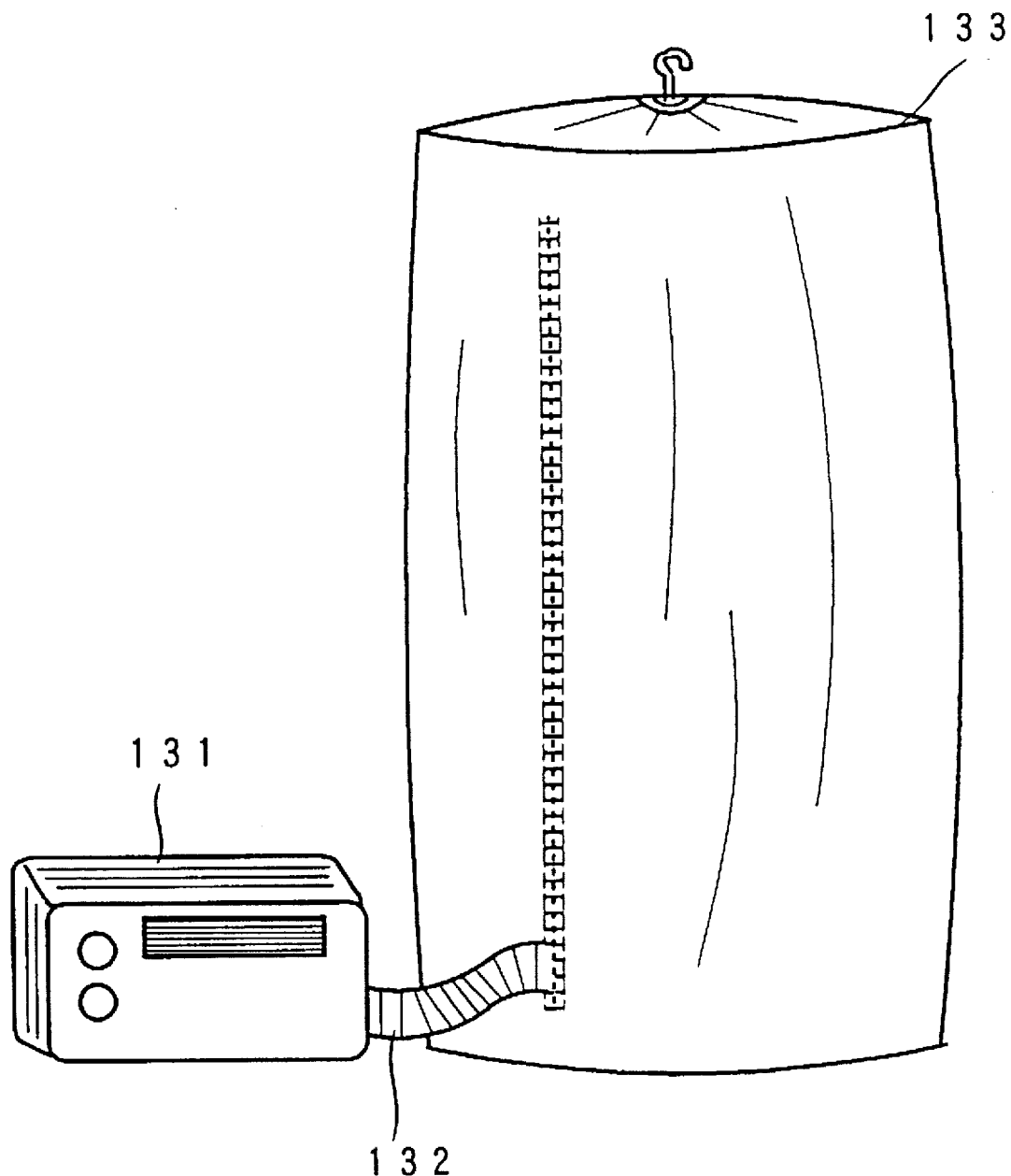
FIG. 21 is a external diagram showing an arrangement of a conventional clothing dryer.

It should be noted that in the device model shown in FIG. 16A the ceramic body is located outside the dryer, and a hose is provided for absorbing the gas in the bag so that the amount of gas that was transmitted to the bag could be adjusted.

The present applicant delegated to Nihon Shokuhin Analysis Center Foundation the performance of the experiments to determine the sterilization effects obtained by the use of the two thus structured dryer models (A and B).

At the Center, *Staphylococcus aureus* ATCC 25923 and *Escherichia coli* NIHJ JC-2 were smeared by about $10^4$ to $10^5$CFU in a sterilization petri dish and placed in the acrylic box.

Then, the device was activated and warn air was transmitted to the acrylic box until the box was filled with the air. The number of living germs in the petri dish was measured by the planar conrage method as time elapsed.

As a result, as is shown in FIG. 17, when 30 minutes had elapsed the staphylococcus aureus count had been reduced to 4.0% and the *escherichia coli* count had been reduced to 12.5% of the counts before the device was activated. After one hour had elapsed, the *staphylococcus aureus* and the *escherichia coli* were reduced to the detection limit or lower ($<1.0 \times 10^1$), and preferable results were acquired.

Experiment 2

Also at the Center, the measurement of the remaining amount of chlorine dioxide was conducted by using the models shown in FIGS. 16A and 16B for the device of the present invention.

In the same manner as in experiment 1, the ceramic body that was impregnated with an alkaline chlorine dioxide solution was provided at a dryer. Alkaline chlorine dioxide gas from the dryer was blown through the small holes in the top of the bag against gauze pads that were attached to the ceiling of an acrylic case. Then, the gauze pads were collected at intervals of 20 minutes, one hour, two hours, and three hours following the activation of the dryer, and were immersed in 10 ml of refined water. Droplets of an Ortho-tolidin solution were added to the immersing fluid, and five minutes later color reaction was detected with the naked eye.

As a result, as is shown in FIG. 18, chlorine dioxide was not detected for the intervals of 20 minutes, one hour, two hours, and three hours following the activation of the dryer model.

From the results of the experiments, since chlorine dioxide does not remain in bedclothes and clothing that are processed by using the apparatus of the present invention, it is obvious that human bodies will not at all be affected by the chlorine dioxide.

Various modes of carrying out the invention are contemplated as being within the scope of the following claims that particularly point out and distinctly claim the subject matter regarded as the invention.

What is claimed is:

1. A deodorization, sterilization and drying apparatus for bedding and clothing, which comprises:
   a warm air generator wherein are provided a warm air nozzle, a heater and a fan, and wherein an alkaline chlorine dioxide gas generator, within which is an alkaline ceramic body that is impregnated with an alkaline chlorine dioxide solution, is located along a flow path of said warm air that is generated in said warm air generator,
   an air-permeable air mattress from which said warm air from said warm air generator is ejected to dry bedclothes, and
   a hose for connecting said air mattress to said warm air generator, whereby said warm air from said warm air generator is brought into contact with said ceramic body so as to supply warm air that contains alkaline chlorine dioxide gas to said air mattress.

2. A deodorization, sterilization and drying apparatus for bedding and clothing according to claim 1, further comprising an air-permeable cover that covers said air-permeable air mattress and bedclothes and clothing.

3. A deodorization, sterilization and drying apparatus for bedding and clothing according to claim 1, wherein said alkaline chlorine dioxide solution that is used to permeate said ceramic body, which is impregnated with said alkaline chlorine dioxide solution, has a calculated chlorine dioxide content of 50 ppm to 1000 ppm.

4. A deodorization, sterilization and drying apparatus, for bedding and clothing, according to claim 1, wherein said alkaline chlorine dioxide gas generator is stored detachably in said warm air generator.

5. A deodorization, sterilization and drying apparatus, for bedding and clothing, according to claim 1, wherein said alkaline chlorine dioxide gas generator is installed outside said warm air generator and is so connected to said hose as to be detachable.

6. A deodorization, sterilization and drying apparatus, for bedding and clothing, according to claim 1, wherein a unit for supplying an alkaline chlorine dioxide solution to said ceramic body is detachably attached to said alkaline chlorine dioxide gas generator, and formed in said ceramic body is a solution supply groove for supplying said alkaline chlorine dioxide solution to a surrounding side portion of said ceramic body.

7. A deodorization, sterilization and drying apparatus, for bedding and clothing, according to claim 1, wherein said alkaline ceramic body is columnar in shape, and in cross section has a plurality of longitudinal through holes.

8. A deodorization, sterilization and drying apparatus, for bedding and clothing, according to claim 1, wherein alkaline ceramic for said alkaline ceramic body contains at least one material selected from a group consisting of animal bone powder, shell powder, limestone powder, and coral powder.

9. A deodorization, sterilization and drying apparatus, for bedding and clothing, according to claim 1, wherein said alkaline ceramic is formed of animal bone powder as the main activated element.

10. A deodorization, sterilization and drying apparatus, for bedding and clothing, according to claim 1, wherein said alkaline ceramic contains at least one ceramic selected from a group consisting of silica gel, alumina, and zeolite.

11. A deodorization, sterilization and drying apparatus for bedding and clothing, which comprises:
    a deodorization, sterilization, and drying case, for bedding and clothing, that is freely opened and closed, wherein are provided air outlets, a clothing rod, and a warm air pipe in which warm air ejection holes are formed,
    a warm air generator wherein are provided a warm air nozzle, a heater and a fan, and wherein an alkaline chlorine dioxide gas generator, within which is an alkaline ceramic body that is impregnated with an alkaline chlorine dioxide solution, is located along a flow path of said warm air that is generated by said warm air generator, and
    a hose for connecting said warm air pipe of said deodorization, sterilization and drying case to said warm air generator, whereby said warm air from said warm air generator is brought into contact with said ceramic body so as to supply warm air that contains alkaline chlorine dioxide gas to said deodorization, sterilization and drying case.

12. A deodorization, sterilization and drying apparatus for bedding and clothing according to claim 11, wherein said alkaline chlorine dioxide solution that is used to permeate said ceramic body, which is impregnated with said alkaline chlorine dioxide solution, has a calculated chlorine dioxide content of 50 ppm to 1000 ppm.

13. A deodorization, sterilization and drying apparatus, for bedding and clothing, according to claim 11, wherein said alkaline chlorine dioxide gas generator is stored detachably in said warm air generator.

14. A deodorization, sterilization and drying apparatus, for bedding and clothing, according to claim 11, wherein said alkaline chlorine dioxide gas generator is installed outside said warm air generator and is so connected to said hose as to be detachable.

15. A deodorization, sterilization and drying apparatus, for bedding and clothing, according to claim 11, wherein a unit for supplying an alkaline chlorine dioxide solution to said ceramic body is detachably attached to said alkaline chlorine dioxide gas generator, and formed in said ceramic body is a solution supply groove for supplying said alkaline chlorine dioxide solution to a surrounding side portion of said ceramic body.

16. A deodorization, sterilization and drying apparatus, for bedding and clothing, according to claim 11, wherein said alkaline ceramic body is columnar in shape, and in cross section has a plurality of longitudinal through holes.

17. A deodorization, sterilization and drying apparatus, for bedding and clothing, according to claim 11, wherein alkaline ceramic for said alkaline ceramic body contains at least one material selected from a group consisting of animal bone powder, shell powder, limestone powder, and coral powder.

18. A deodorization, sterilization and drying apparatus, for bedding and clothing, according to claim 11, wherein said alkaline ceramic is formed of animal bone powder as the main activated element.

19. A deodorization, sterilization and drying apparatus, for bedding and clothing, according to claim 11, wherein said alkaline ceramic contains at least one ceramic selected from a group consisting of silica gel, alumina, and zeolite.

20. A deodorization, sterilization and drying apparatus, for medical bedding and clothing, comprising:

- a warm air generator that includes a fan, a heater and an alkaline chlorine dioxide gas generator in which is provided a ceramic body that is impregnated with an alkaline chlorine dioxide solution;
- a non-air-permeable bag, which is freely opened and closed and inside which bedclothes are retained for deodorization, sterilization, and drying;
- a warm air supply pipe, along which warm air that contains alkaline chlorine dioxide gas is supplied from said warm air generator, said warm air being injected into said bag through a plurality of warm air injection holes that are formed in said warm air supply pipe toward the inside of said bag;
- a warm air absorption pipe for absorbing said warm air after bedclothes in said bag are deodorized, sterilized and dried; and
- a warm air filter, which has a replaceable filter medium and a replaceable adjusting filter medium, for filtering said warm air that is directed through said warm air absorption pipe after deodorization, sterilization and drying are completed, and for discharging said filtered air to the outside.

21. A deodorization, sterilization and drying apparatus, for medical bedding and clothing, according to claim 20, wherein said alkaline chlorine dioxide solution that is used to permeate said ceramic body, which is impregnated with said alkaline chlorine dioxide solution, has a calculated chlorine dioxide content of 500 ppm to 3000 ppm.

22. A deodorization, sterilization and drying apparatus, for medical bedding and clothing, according to claim 20, wherein said filter medium, which is replaceably provided in said warm air filter, is comprised of at least one of non-woven cloth and activated carbon, and said adjusting filter medium is comprised of ceramic particles.

23. A deodorization, sterilization and drying apparatus, for medical bedding and clothing, according to claim 20, wherein said alkaline chlorine dioxide gas generator is stored detachably in said warm air generator.

24. A deodorization, sterilization and drying apparatus, for medical bedding and clothing, according to claim 20, wherein said alkaline chlorine dioxide gas generator is installed outside said warm air generator and is so connected to said pipe as to be detachable.

25. A deodorization, sterilization and drying apparatus, for medical bedding and clothing, according to claim 20, wherein a unit for supplying an alkaline chlorine dioxide solution to said ceramic body is detachably attached to said alkaline chlorine dioxide gas generator, and formed in said ceramic body is a solution supply groove for supplying said alkaline chlorine dioxide solution to a surrounding side portion of said ceramic body.

26. A deodorization, sterilization and drying apparatus, for medical bedding and clothing, according to claim 20, wherein said alkaline ceramic body is columnar in shape, and in cross section has a plurality of longitudinal through holes.

27. A deodorization, sterilization and drying apparatus for, medical bedding and clothing, according to claim 20, wherein alkaline ceramic for said alkaline ceramic body contains at least one material selected from a group consisting of animal bone powder, shell powder, limestone powder, and coral powder.

28. A deodorization, sterilization and drying apparatus for, medical bedding and clothing, according to claim 20, wherein said alkaline ceramic is formed of animal bone powder as the main activated element.

29. A deodorization, sterilization and drying apparatus for, medical bedding and clothing, according to claim 20, wherein said alkaline ceramic contains at least one ceramic selected from a group consisting of silica gel, alumina, and zeolite.

* * * * *